(12) United States Patent
Figura et al.

(10) Patent No.: US 9,433,571 B2
(45) Date of Patent: Sep. 6, 2016

(54) IRRITATION MITIGATING POLYMERS AND USES THEREFOR

(71) Applicant: Lubrizol Advanced Materials, Inc., Cleveland, OH (US)

(72) Inventors: Brian D. Figura, Cleveland, OH (US); Krishnan Chari, Hudson, OH (US); Wei-Yeih Yang, Brecksville, OH (US)

(73) Assignee: Lubrizol Advanced Materials, Inc., Cleveland, OH (US)

( * ) Notice: Subject to any disclaimer, the term of this patent is extended or adjusted under 35 U.S.C. 154(b) by 0 days.

(21) Appl. No.: 14/653,491

(22) PCT Filed: Dec. 12, 2013

(86) PCT No.: PCT/US2013/074586
§ 371 (c)(1),
(2) Date: Jun. 18, 2015

(87) PCT Pub. No.: WO2014/099585
PCT Pub. Date: Jun. 26, 2014

(65) Prior Publication Data
US 2015/0342860 A1    Dec. 3, 2015

Related U.S. Application Data

(60) Provisional application No. 61/739,830, filed on Dec. 20, 2012.

(51) Int. Cl.
| | | |
|---|---|---|
| *A61Q 5/02* | (2006.01) | |
| *A61Q 19/10* | (2006.01) | |
| *C11D 1/90* | (2006.01) | |
| *A61K 8/81* | (2006.01) | |
| *C11D 1/14* | (2006.01) | |
| *A61K 8/44* | (2006.01) | |
| *A61K 8/46* | (2006.01) | |
| *C11D 3/00* | (2006.01) | |
| *C11D 3/37* | (2006.01) | |

(52) U.S. Cl.
CPC ............ *A61K 8/8176* (2013.01); *A61K 8/442* (2013.01); *A61K 8/463* (2013.01); *A61K 8/8182* (2013.01); *A61Q 5/02* (2013.01); *A61Q 19/10* (2013.01); *C11D 1/143* (2013.01); *C11D 1/90* (2013.01); *C11D 3/0005* (2013.01); *C11D 3/3776* (2013.01); *A61K 2800/5422* (2013.01); *A61K 2800/75* (2013.01)

(58) Field of Classification Search
None
See application file for complete search history.

(56) References Cited

U.S. PATENT DOCUMENTS 5,605,685 A    2/1997  Tseng et al.

FOREIGN PATENT DOCUMENTS

| WO | 91/16037 A1 | 10/1991 |
|---|---|---|
| WO | 2005/023970 A1 | 3/2005 |
| WO | 2008/060997 A1 | 5/2008 |
| WO | 2011/042379 A1 | 4/2011 |
| WO | 2013/040174 A1 | 9/2012 |
| WO | 2013/040167 A1 | 3/2013 |
| WO | 2013/040178 A1 | 3/2013 |
| WO | 2013/054760 A1 | 4/2013 |
| WO | 2014/099573 A1 | 6/2014 |

*Primary Examiner* — Yevegeny Valenrod
(74) *Attorney, Agent, or Firm* — Thoburn T. Dunlap

(57) ABSTRACT

The present invention provides mild cleansing and cleaning compositions and methods for mitigating irritation induced by harsh detersive surfactants. The invention relates to a method of reducing skin irritation associated with a cleansing composition comprising at least one surfactant, the method comprising combining an effective amount of at least one nonionic amphiphilic polymer with at least one detersive surfactant selected from anionic surfactants, amphoteric surfactants, nonionic surfactants and combinations of two or more thereof. The at least one nonionic amphiphilic irritation mitigating polymer is prepared from a free radically polymerizable monomer composition comprising at least one hydrophilic monomer and at least one hydrophobic monomer, wherein said N-vinyl lactam and wherein said hydrophobic monomer is selected from a vinyl ester of a $C_1$-$C_{22}$ carboxylic acid or at least one monomer selected from a $C_8$-$C_{22}$ alkyl (meth)acrylate an associative monomer, a semi-hydrophobic monomer, or mixtures thereof.

15 Claims, No Drawings

IRRITATION MITIGATING POLYMERS AND USES THEREFOR

CROSS REFERENCE TO RELATED APPLICATION

This application claims priority from PCT Application Serial No. PCT/US2013/074586 filed on Dec. 12, 2013, which claims the benefit of U.S. Provisional Application No. 61/739,830 filed on Dec. 20, 2012.

FIELD OF THE INVENTION

In one aspect, the present invention relates to linear and crosslinked nonionic amphiphilic polymers and their use as ocular and/or dermal irritation mitigants in surfactant containing compositions. The crosslinked nonionic amphiphilic polymers of the invention are advantageous because they also provide tailored yield stress properties to cleansing formulations across a wide pH range. Exemplary embodiments of the invention relate to a method for mitigating irritation of the skin and eyes in surfactant containing personal care cleansing compositions, pet care cleansing compositions, household care cleaning compositions, and reduced irritation industrial and institutional care cleaning compositions by including therein the linear and/or crosslinked nonionic amphiphilic polymers of the invention.

BACKGROUND

Detersive agents such as anionic, cationic, amphoteric and nonionic surfactants are widely used in aqueous based cleansing formulations. In personal care cleansing products (e.g., shampoos, body washes, facial cleansers, liquid hand soaps, hand wipes, etc.), pet care products (e.g., shampoos), household care cleaning products (e.g., hard surface cleaners, laundry detergents, dish soaps, automatic dish washer detergents, shower and bathtub cleansers, bathroom cleansers, car wash detergents, etc.) and industrial and institutional care cleaners (high strength cleaners, detergents, etc.) the surfactant package is the most important component in the detersive formulation. These compositions generally comprise a mixture of one or more surfactants as the active detersive ingredient. The surfactant: 1) improves the wettability of the soiled substrate; 2) loosens soils/oils/sebum from the substrate; and 3) emulsifies, solubilizes and/or suspends the loosened soils/oils/sebum particles in the aqueous wash medium.

Although in principle any surfactant class (e.g., cationic, anionic, nonionic, amphoteric) is suitable as the detersive agent in cleansing or cleaning applications, in practice most personal care cleansers and household cleaning products are formulated with anionic surfactants or with a combination of an anionic surfactant as the primary detersive agent with one or more secondary surfactants selected from the other surfactant classes. Anionic surfactants are used as one of detersive agents in personal care cleansers and detergent cleaning products because of their superior detersive properties. Exemplary anionic surfactants traditionally utilized in these formulations include alkyl sulfates, alkyl benzene sulfonates, and olefin sulfonates. While the anionic surfactants and in particular the anionic sulfates and sulfonates are very efficient detersive agents, they tend to be irritating to the skin and eyes at concentrations typically utilized for efficient detergency. It is widely known that anionic surfactants are adsorbed and even penetrate into the top layers of the skin resulting in irritation to the skin. This irritation is characteristically expressed by reddening of the skin, chapping, scaling, rash development, itching and, in extreme cases, cracking of the skin, or a burning sensation in the eyes.

It has become more and more important to consumers that aqueous cleansing compositions are efficient cleansers as well as mild. These combined properties are especially useful if the cleansing compositions are to be in direct contact with the hair and skin. Consequently, efforts have been made by formulators to deliver personal care cleansing products, household detergents and cleaners and institutional and industrial cleaners that have these properties.

Attempts to impart mildness to cleansers, particularly those formulated for personal care use, involved careful selection of the surfactants employed in the product. It is known that the irritation caused by anionic sulfates can be reduced by introducing ethoxylation into the surfactant molecule. However, a reduction in irritation is accompanied by a corresponding reduction in detergency. For example, sodium lauryl sulfate, a highly detersive surfactant, causes significant eye irritation. In contrast, sodium laureth-12 sulfate (the corresponding ethoxylate containing 12 moles of ethoxylation) is almost completely non-irritating, but is a poor detersive agent (see Schoenberg, "Baby Shampoo," Household & Personal Products Industry 60 (September 1979)). The poor detersive properties of ethoxylated alkyl sulfates are reported in many other publications.

Additional attempts to attenuate the adverse irritant effects of anionic surfactants have been made by replacing some of the anionic surfactant with very mild secondary surfactants such as amphoteric and/or nonionic surfactants as disclosed in U.S. Pat. No. 4,726,915. However, reducing the amount of anionic surfactant in a cleansing or cleaning composition adversely affects the detersive properties of the composition. The major problem in providing such products resides in the fact that both properties (efficient detergency and mildness) tend to be mutually incompatible. While highly detersive surfactants are generally very harsh, mild surfactants tend to provide insufficient detersive properties.

Another approach for attenuating the adverse irritant effects of anionic detersive surfactants while maintaining high detersive properties in personal care cleansing compositions is disclosed in International Patent Application Pub. No. WO 2005/023970. It is disclosed that certain hydrophobically modified polymeric materials capable of binding surfactant can be combined with anionic surfactants to produce personal care compositions that exhibit relatively low ocular and/or dermal irritation while maintaining high detersive properties. Disclosed hydrophobically modified materials include hydrophobically modified crosslinked acrylic copolymers that are synthesized from at least one ethylenically unsaturated carboxylic acid monomer and at least one ethylenically unsaturated hydrophobically modified monomer. Exemplary hydrophobically modified acrylic polymers are set forth in U.S. Pat. No. 6,433,061 to Noveon, Inc. (now Lubrizol Advanced Materials, Inc.). The disclosure additionally exemplifies polymers available under the trade names Carbopol® Aqua SF-1 and Carbopol® ETD 2020 both provided by Lubrizol Advanced Materials, Inc. as suitable polymers for use as a surfactant binder.

In Pub. No. WO 2005/023970 the applicants therein disclose a relationship between the critical micelle concentration (CMC) of an anionic surfactant in solution and the tendency of the surfactant to induce irritation. The CMC is illustrated by curve 11 in FIG. 1 of the WO 2005/023970 disclosure. As the surfactant is sequentially dosed into a container (of standardized dimension) of water the surfactant initially occupies the surface (liquid/air interface) of the water/surfactant solution. With each sequential dose of surfactant there is a concomitant reduction in the surface tension of the solution until essentially all of the interfacial surface area is filled. Continued dosing of surfactant results in the formation of micelles within the solution. The surfactant concentration at which the further addition of surfactant does not elicit any appreciable affect in solution surface tension is defined as the CMC (point 12 of curve 11). Additional surfactant added after the CMC has been attained was found to induce irritation. In contrast, as illustrated in curve 15 of FIG. 1, as anionic surfactant is added to an aqueous solution comprising a hydrophobically modified crosslinked acrylic polymeric material, the CMC is shifted to a significantly higher surfactant concentration. Accordingly, the inclusion of hydrophobically modified crosslinked acrylic copolymers allows the use of higher concentrations of anionic surfactant in cleansing and cleaning compositions without the attendant ocular and dermal irritation effects.

It is to be noted that the polymers disclosed in U.S. Pat. No. 6,433,061 as well as the polymers identified under the Carbopol® Aqua SF-1 and ETD 2020 trade names are rheology modifiers which thicken or enhance the rheology of the composition in which they are included. In the trade literature Carbopol® Aqua SF-1 polymer is described by Lubrizol Advanced Materials, Inc. Technical Data Sheet TDS-294 (July, 2003) as: " . . . a lightly crosslinked acrylic polymer dispersion designed to impart suspending, stabilizing, and thickening properties to a variety of surfactant-based personal cleansing products". The foregoing acrylic based polymers are non-linear (crosslinked), branched polymer chains which interconnect to form three dimensional network structures and have long been used in personal care applications for their rheological and structure building properties. Upon neutralization, these water soluble or dispersible polymers possess the unique ability to greatly increase the viscosity of the liquid in which they are dissolved or dispersed.

The disclosed hydrophobically modified crosslinked acrylic copolymers are viscosity building agents that increase the viscosity of compositions in which they are dissolved or dispersed upon suitable neutralization of the carboxylic acid moieties on the polymer backbone with an alkaline material. As increasing amounts of viscosity builder are added to a cleansing or cleaning formulation to mitigate the adverse irritation effects of the anionic surfactant there is a corresponding increase in the viscosity of the composition. It is well known in the personal care, household care and industrial and institutional care formulation art that a liquid cleanser or cleaner should have an ideal viscosity. Indeed, viscosity allows for the controlled handling and dispensing of the product during use as compared to a thinner product. In personal care cleansing applications, a thick, rich shampoo or body cleanser is appealing to consumers from a sensory perspective. In household care applications, viscosity permits a better efficacy of the product when applied to non-horizontal surfaces such as toilet bowls, sinks, shower stalls, bath tubs, and the like. In addition, cleansing and cleaning products are expected to be easy to use. In other words, the shear thinning profile of the liquid composition should exhibit high viscosity at low shear conditions and lower viscosity at high shear conditions to aid in the application and removal of the product from the substrate to be cleaned.

The commercially available Carbopol® SF-1 polymer and similar polymers comprise a chemically crosslinked backbone having a pH-responsive functionality that is either base or acid sensitive. The polymers may be mixed with other ingredients in a formulation and then neutralized by the addition of a neutralization agent such as an acid or a base. Acid sensitive thickeners are activated upon contact with an acidic agent, while base-sensitive thickeners are activated upon contact with an alkaline agent. Upon neutralization, the polymers swell significantly to form a randomly close-packed (RCP) jammed network of swollen cross-linked micro-gel particles imparting a desired rheological profile, i.e., yield stress, elastic modulus, and viscosity, as well as optical clarity to the formulation.

There are drawbacks associated with increasing the viscosity of a product beyond its ideal viscosity. Highly viscous products are typically difficult to apply and rinse away, especially if the shear thinning profile of the viscosity building agent is poor. High viscosities can also adversely affect packaging, dispensing, dissolution, and the foaming and sensory properties of the product.

While a certain rheology modifier may thicken or enhance the viscosity of a composition in which it is included, it does not necessarily have desirable yield stress properties. A desirable yield stress property is critical to achieving certain physical and aesthetic characteristics in a liquid medium, such as the indefinite suspension of particles, insoluble liquid droplets, or the stabilization of gas bubbles within a liquid medium. Particles dispersed in a liquid medium will remain suspended if the yield stress (yield value) of the medium is sufficient to overcome the effect of gravity or buoyancy on those particles. Insoluble liquid droplets can be prevented from rising and coalescing and gas bubbles can be suspended and uniformly distributed in a liquid medium using yield value as a formulating tool. A yield stress fluid is used generally to adjust or modify the rheological properties of aqueous compositions. Such properties include, without limitation, viscosity improvement, flow rate improvement, stability to viscosity change over time, and the ability to suspend particles for indefinite periods of time.

To alleviate the substantial viscosity profile of the above described crosslinked hydrophobically modified acrylic polymers, U.S. Pat. No. 8,293,845 describes the use of low molecular weight hydrophobically modified linear (non-crosslinked) acrylic polymers to increase the CMC of a surfactant containing composition to mitigate irritation. The applicants teach that the ideal CMC is achieved by neutralizing the linear polymer with an alkaline material to a degree of neutralization ranging from about 15 to about 30%, based on the acid number of the polymer. As with the crosslinked hydrophobically modified acrylic polymer irritation mitigants, these linear acrylic polymer counterparts are pH dependent in that the degree of neutralization of the polymer must be maintained within a narrow range in order to reach the optimal CMC value. In addition, the disclosed linear polymers are not crosslinked and do not create a yield stress.

Accordingly, there is a need for an irritation mitigation polymer that is not pH dependent and that can be tailored to create a desired yield stress in the detersive composition in which it is incorporated.

SUMMARY OF THE INVENTION

The present invention provides mild cleansing and cleaning compositions and methods for mitigating irritation induced by harsh detersive surfactants contained therein. It has been discovered that a milder cleansing composition possessing excellent detersive properties can be obtained by incorporating at least one nonionic amphiphilic polymer into the formulation to mitigate the irritant effects of harsh detersive surfactants contained therein.

It has been discovered that the nonionic, amphiphilic polymers of the invention exhibit a unique and unexpected combination of properties including the ability to mitigate irritation in and to provide yield stress properties to surfactant containing cleansing and cleaning compositions that is independent of pH.

In one aspect, the invention provides mild cleansing and cleaning compositions comprising at least one nonionic amphiphilic polymer and at least one detersive surfactant selected from anionic surfactants, amphoteric surfactants, nonionic surfactants and combinations of two or more thereof.

In another aspect, an embodiment of the invention relates to a method of reducing skin irritation associated with a cleansing composition comprising at least one surfactant, the method comprising combining a nonionic amphiphilic polymer with at least one detersive surfactant selected from anionic surfactants, amphoteric surfactants, nonionic surfactants and combinations of two or more thereof.

In another aspect, the invention relates to a method of reducing skin irritation induced by a surfactant containing composition the method comprises the step of contacting a mammalian body with a detersive composition comprising at least one nonionic amphiphilic polymer and at least one detersive surfactant selected from anionic surfactants, amphoteric surfactants, nonionic surfactants and combinations of two or more thereof.

In another aspect, the at least one nonionic amphiphilic polymer capable of mitigating irritation to the eyes and skin in surfactant containing compositions comprising at least one surfactant selected from anionic surfactants, amphoteric surfactants, nonionic surfactants and combinations of two or more thereof is not pH dependent and can be tailored to provide desired yield stress properties to a given detersive surfactant containing cleansing and cleaning formulation.

In another aspect, an embodiment of the invention relates to a method of reducing skin irritation associated with a thickened cleansing composition comprising at least one surfactant, the method comprising combining a crosslinked, nonionic amphiphilic polymer with at least one detersive surfactant selected from anionic surfactants, amphoteric surfactants, nonionic surfactants and combinations of two or more thereof, wherein the concentration of the amphiphilic polymer is no more than 5 wt. %, and the at least one surfactant is no more than 30 wt. % (all weight percents are based on the total weight of the composition), wherein the yield stress of the composition is at least 0.1 Pa with a shear thinning index of less than 0.5 at shear rates between about 0.1 and about 1 reciprocal seconds, and wherein the yield stress, elastic modulus and optical clarity of the composition are substantially independent of pH in the range of about 2 to about 14.

In another aspect, an embodiment of the invention relates to a method of reducing skin irritation associated with a thickened cleansing composition comprising at least one surfactant, the method comprising combining a crosslinked, nonionic amphiphilic polymer with at least one detersive surfactant selected from anionic surfactants, amphoteric surfactants, nonionic surfactants and combinations of two or more thereof, wherein the concentration of the amphiphilic polymer is no more than 5 wt. %, and the at least one surfactant is no more than 30 wt. % (all weight percents are based on the total weight of the composition), wherein the yield stress of the composition is at least 0.1 Pa with a shear thinning index of less than 0.5 at shear rates between about 0.1 and about 1 reciprocal seconds, wherein the yield stress, elastic modulus of the composition are substantially independent of pH in the range of about 2 to about 14, and wherein the composition is able to suspend beads of a size between 0.5 and 1.5 mm where the difference in specific gravity of the beads relative to water is in the range of 0.2 to 0.5 for a period of at least 4 weeks at room temperature.

In one aspect of the present invention, the at least one nonionic amphiphilic irritation mitigating polymer is prepared from a free radically polymerizable monomer composition comprising at least one hydrophilic monomer and at least one hydrophobic monomer. In one embodiment the hydrophilic monomer is selected from hydroxy($C_1$-$C_5$)alkyl (meth)acrylates, N-vinyl amides, amino group containing monomers, or mixtures thereof. In one embodiment the hydrophobic monomer is selected from esters of (meth) acrylic acid with alcohols containing 1 to 30 carbon atoms, vinyl esters of aliphatic carboxylic acids containing 1 to 22 carbon atoms, vinyl ethers of alcohols containing 1 to 22 carbon atoms, vinyl aromatic monomers, vinyl halides, vinylidene halides, associative monomers, semi-hydrophobic monomers, or mixtures thereof.

In one aspect of the present invention, the at least one nonionic amphiphilic irritation mitigating polymer is prepared from a free radically polymerizable monomer composition comprising at least one hydrophilic monomer, at least one hydrophobic monomer, and at least one crosslinking monomer. In one embodiment, the hydrophilic monomer is selected from hydroxy($C_1$-$C_5$)alkyl(meth)acrylates, N-vinyl amides, amino group containing monomers, or mixtures thereof. In one embodiment, the hydrophobic monomer is selected from esters of (meth)acrylic acid with alcohols containing 1 to 30 carbon atoms, vinyl esters of aliphatic carboxylic acids containing 1 to 22 carbon atoms, vinyl ethers of alcohols containing 1 to 22 carbon atoms, vinyl aromatic monomers, vinyl halides, vinylidene halides, associative monomers, semi-hydrophobic monomers, or mixtures thereof. In one embodiment, the crosslinking monomer is selected from at least one polyunsaturated monomer containing at least two polymerizable unsaturated moieties.

The nonionic, amphiphilic polymer compositions as well as the thickened aqueous fluid comprising the nonionic, amphiphilic, polymer compositions and the at least one surfactant of the present invention may suitably comprise, consist of, or consist essentially of the components, elements, and process delineations described herein. The invention illustratively disclosed herein suitably may be practiced in the absence of any element or process step which is not specifically disclosed herein.

Unless otherwise stated, all percentages, parts, and ratios expressed herein are based upon the total weight of the components contained in the compositions of the present invention.

As used herein, the term "amphiphilic polymer" means that the polymeric material has distinct hydrophilic and hydrophobic portions. "Hydrophilic" typically means a portion that interacts intramolecularly with water and other polar molecules. "Hydrophobic" typically means a portion that interacts preferentially with oils, fats or other non-polar molecules rather than aqueous media.

As used herein, the term "hydrophilic monomer" means a monomer that is substantially water soluble. "Substantially water soluble" refers to a material that is soluble in distilled (or equivalent) water, at 25° C., at a concentration of about 3.5% by weight in one aspect, and soluble at about 10% by weight in another aspect (calculated on a water plus monomer weight basis).

As used herein, the term "hydrophobic monomer" means a monomer that is substantially water insoluble. "Substantially water insoluble" refers to a material that is not soluble in distilled (or equivalent) water, at 25° C., at a concentration of about 3% by weight in one aspect, and not soluble at about 2.5% by weight in another aspect (calculated on a water plus monomer weight basis).

By "nonionic" is meant that a monomer, monomer composition or a polymer polymerized from a monomer composition is devoid of ionic or ionizable moieties ("nonionizable").

An ionizable moiety is any group that can be made ionic by neutralization with an acid or a base.

An ionic or an ionized moiety is any moiety that has been neutralized by an acid or a base.

By "substantially nonionic" is meant that the monomer, monomer composition or polymer polymerized from a monomer composition contains less than 5 wt. % in one aspect, less than 3 wt. % in another aspect, less than 1 wt. % in a further aspect, less than 0.5 wt. % in a still further aspect, less than 0.1 wt. % in an additional aspect, and less than 0.05 wt. % in a further aspect, of an ionizable and/or an ionized moiety.

For the purpose of the specification, the prefix "(meth) acryl" includes "acryl" as well as "methacryl". For example, the term "(meth)acrylamide" includes both acrylamide and methacrylamide.

DESCRIPTION OF EXEMPLARY EMBODIMENTS

Exemplary embodiments in accordance with the present invention will be described. Various modifications, adaptations or variations of the exemplary embodiments described herein may become apparent to those skilled in the art as such are disclosed. It will be understood that all such modifications, adaptations or variations that rely upon the teachings of the present invention, and through which these teachings have advanced the art, are considered to be within the scope and spirit of the present invention.

While overlapping weight ranges for the various components and ingredients that can be contained in the compositions of the invention have been expressed for selected embodiments and aspects of the invention, it should be readily apparent that the specific amount of each component in the disclosed compositions will be selected from its disclosed range such that the amount of each component is adjusted such that the sum of all components in the composition will total 100 weight percent. The amounts employed will vary with the purpose and character of the desired product and can be readily determined by one skilled in the art.

Amphiphilic Polymer

The nonionic, amphiphilic polymers useful in the practice of the invention are polymerized from monomer components that contain free radical polymerizable unsaturation. In one embodiment, the nonionic, amphiphilic polymers useful in the practice of the invention are polymerized from a monomer composition comprising at least one nonionic, hydrophilic unsaturated monomer, and at least one unsaturated hydrophobic monomer. In another embodiment, the nonionic, amphiphilic polymers useful in the practice of the invention are crosslinked. The crosslinked polymers are prepared from a monomer composition comprising at least one nonionic, hydrophilic unsaturated monomer, at least one unsaturated hydrophobic monomer, and at least one polyunsaturated crosslinking monomer.

In one embodiment, the copolymers can be prepared from a monomer composition typically having a hydrophilic monomer to hydrophobic monomer ratio of from about 5:95 wt. % to about 95:5 wt. % in one aspect, from about 15:85 wt. % to about 85:15 wt. % in another aspect, and from about 30:70 wt. % to about 70:30 wt. % in a further aspect, based on the total weight of the hydrophilic and hydrophobic monomers present. The hydrophilic monomer component can be selected from a single hydrophilic monomer or a mixture of hydrophilic monomers, and the hydrophobic monomer component can be selected from a single hydrophobic monomer or a mixture of hydrophobic monomers.

Hydrophilic Monomer

Representative hydrophilic monomers include but are not limited to open chain and cyclic N-vinylamides (N-vinyl lactams containing 4 to 9 atoms in the lactam ring moiety, wherein the ring carbon atoms optionally can be substituted by one or more lower alkyl groups such as methyl, ethyl or propyl); hydroxy($C_1$-$C_5$)alkyl(meth)acrylates; amino group containing vinyl monomers selected from (meth)acrylamide, N—($C_1$-$C_5$)alkyl(meth)acrylamides, N,N-di($C_1$-$C_5$)alkyl(meth)acrylamides, N—($C_1$-$C_5$)alkylamino($C_1$-$C_5$)alkyl(meth)acrylamides and N,N-di($C_1$-$C_5$)alkylamino($C_1$-$C_5$)alkyl(meth)acrylamides, wherein the alkyl moieties on the disubstituted amino groups can be the same or different, and wherein the alkyl moieties on the monosubstituted and disubstituted amino groups can be optionally substituted with a hydroxyl group; other monomers include vinyl alcohol; vinyl imidazole; and (meth)acrylonitrile. Mixtures of the foregoing monomers also can be utilized.

Representative open chain N-vinylamides include N-vinylformamide, N-methyl-N-vinylformamide, N-(hydroxymethyl)-N-vinylformamide, N-vinylacetamide, N-vinylmethylacetamide, N-(hydroxymethyl)-N-vinylacetamide, and mixtures thereof. Additionally, monomers containing a pendant N-vinyl lactam moiety can also be employed, e.g., N-vinyl-2-ethyl-2-pyrrolidone (meth)acrylate.

Representative cyclic N-vinylamides (also known as N-vinyl lactams) include N-vinyl-2-pyrrolidinone, N-(1-methyl vinyl) pyrrolidinone, N-vinyl-2-piperidone, N-vinyl-2-caprolactam, N-vinyl-5-methyl pyrrolidinone, N-vinyl-3,3-dimethyl pyrrolidinone, N-vinyl-5-ethyl pyrrolidinone and N-vinyl-6-methyl piperidone, and mixtures thereof.

The hydroxy($C_1$-$C_5$)alkyl(meth)acrylates can be structurally represented by the following formula:

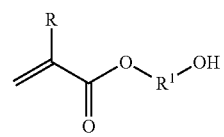

(I)

wherein R is hydrogen or methyl and $R^1$ is an divalent alkylene moiety containing 1 to 5 carbon atoms, wherein the alkylene moiety optionally can be substituted by one or more methyl groups. Representative monomers include 2-hydroxyethyl(meth)acrylate, 3-hydroxypropyl(meth)acrylate, 4-hydroxybutyl(meth)acrylate, and mixtures thereof.

The amino group containing vinyl monomers include (meth)acrylamide, diacetone acrylamide and monomers that are structurally represented by the following formulas:

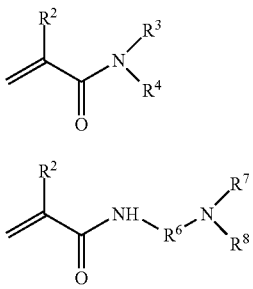

(II)

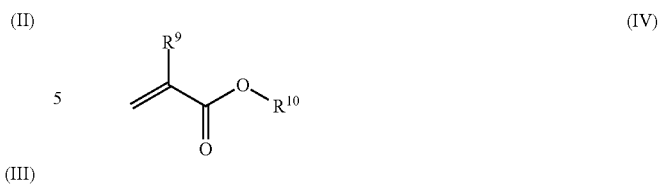

(IV)

(III)

wherein $R^9$ is hydrogen or methyl and $R^{10}$ is $C_1$ to $C_{30}$ alkyl. Representative monomers under formula (IV) include but are not limited to methyl(meth)acrylate, ethyl(meth)acrylate, butyl(meth)acrylate, sec-butyl(meth)acrylate, iso-butyl (meth)acrylate, hexyl(meth)acrylate), heptyl(meth)acrylate, octyl(meth)acrylate, 2-ethylhexyl(meth)acrylate, decyl (meth)acrylate, isodecyl(meth)acrylate, lauryl(meth)acrylate, tetradecyl(meth)acrylate, hexadecyl(meth)acrylate, stearyl(meth)acrylate, behenyl(meth)acrylate, and mixtures thereof.

Formula (II) represents N—($C_1$-$C_5$)alkyl(meth)acrylamide or N,N-di($C_1$-$C_5$)alkyl(meth)acrylamide wherein $R^2$ is hydrogen or methyl, $R^3$ independently is selected from hydrogen, $C_1$ to $C_5$ alkyl and $C_1$ to $C_5$ hydroxyalkyl, and $R^4$ independently is selected from is $C_1$ to $C_5$ alkyl or $C_1$ to $C_5$ hydroxyalkyl.

Formula (III) represents N—($C_1$-$C_5$)alkylamino($C_1$-$C_5$) alkyl(meth)acrylamide or N,N-di($C_1$-$C_5$)alkylamino($C_1$-$C_5$) alkyl(meth)acrylamide wherein $R^5$ is hydrogen or methyl, $R^6$ is $C_1$ to $C_5$ alkylene, $R^7$ independently is selected from hydrogen or $C_1$ to $C_5$ alkyl, and $R^8$ independently is selected from $C_1$ to $C_5$ alkyl.

Vinyl esters of aliphatic carboxylic acids containing 1 to 22 carbon atoms can be represented by the following formula:

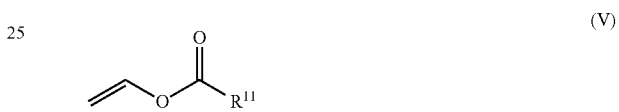

(V)

Representative N-alkyl(meth)acrylamides include but are not limited to N-methyl(meth)acrylamide, N-ethyl(meth) acrylamide, N-propyl(meth)acrylamide, N-isopropyl(meth) acrylamide, N-tert-butyl(meth)acrylamide, N-(2-hydroxyethyl)(meth)acrylamide, N-(3-hydroxypropyl)(meth) acrylamide, and mixtures thereof.

wherein $R^{11}$ is a $C_1$ to $C_{22}$ aliphatic group which can be an alkyl or alkenyl. Representative monomers under formula (V) include but are not limited to vinyl acetate, vinyl propionate, vinyl butyrate, vinyl isobutyrate, vinyl valerate, vinyl hexanoate, vinyl 2-methylhexanoate, vinyl 2-ethylhexanoate, vinyl iso-octanoate, vinyl nonanoate, vinyl neodecanoate, vinyl decanoate, vinyl versatate, vinyl laurate, vinyl palmitate, vinyl stearate, and mixtures thereof.

Representative N,N-dialkyl(meth)acrylamides include but are not limited to N,N-dimethyl(meth)acrylamide, N,N-diethyl(meth)acrylamide, N,N-(di-2-hydroxyethyl)(meth) acrylamide, N,N-(di-3-hydroxypropyl)(meth)acrylamide, N-methyl, N-ethyl(meth)acrylamide, and mixtures thereof.

Representative N,N-dialkylaminoalkyl(meth)acrylamides include but are not limited to N,N-dimethylaminoethyl (meth)acrylamide, N,N-diethylaminoethyl(meth)acrylamide, N,N-dimethylaminopropyl(meth)acrylamide, and mixtures thereof.

In one aspect, the vinyl ethers of alcohols containing 1 to 22 carbon atoms can be represented by the following formula:

Hydrophobic Monomer

Hydrophobic monomers suitable for the preparation of the crosslinked, nonionic, amphiphilic polymer compositions of the invention are selected from but are not limited to one or more of alkyl esters of (meth)acrylic acid having an alkyl group containing 1 to 30 carbon atoms; vinyl esters of aliphatic carboxylic acids containing 1 to 22 carbon atoms; vinyl ethers of alcohols containing 1 to 22 carbon atoms; vinyl aromatics containing 8 to 20 carbon atoms; vinyl halides; vinylidene halides; linear or branched alpha-monoolefins containing 2 to 8 carbon atoms; an associative monomer having a hydrophobic end group containing 8 to 30 carbon atoms, and mixtures thereof.

(VI)

wherein $R^{13}$ is a $C_1$ to $C_{22}$ alkyl. Representative monomers of formula (VI) include methyl vinyl ether, ethyl vinyl ether, butyl vinyl ether, isobutyl vinyl ether, 2-ethylhexyl vinyl ether, decyl vinyl ether, lauryl vinyl ether, stearyl vinyl ether, behenyl vinyl ether, and mixtures thereof.

Representative vinyl aromatic monomers include but are not limited to styrene, alpha-methylstyrene, 3-methyl styrene, 4-methyl styrene, 4-propyl styrene, 4-tert-butyl styrene, 4-n-butyl styrene, 4-n-decyl styrene, vinyl naphthalene, and mixtures thereof.

Semi-Hydrophobic Monomer

Optionally, at least one semi-hydrophobic monomer can be used in the preparation of the amphiphilic polymers of the invention. A semi-hydrophobic monomer is similar in structure to an associative monomer, but has a substantially non-hydrophobic end group selected from hydroxyl or a moiety containing 1 to 4 carbon atoms.

Representative vinyl and vinylidene halides include but are not limited to vinyl chloride and vinylidene chloride, and mixtures thereof.

Representative alpha-olefins include but are not limited to ethylene, propylene, 1-butene, iso-butylene, 1-hexene, and mixtures thereof.

In one aspect of the invention, alkyl esters of (meth) acrylic acid having an alkyl group containing 1 to 30 carbon atoms can be represented by the following formula:

The associative monomer of the invention has an ethylenically unsaturated end group portion (i) for addition polymerization with the other monomers of the invention; a polyoxyalkylene mid-section portion (ii) for imparting selective hydrophilic and/or hydrophobic properties to the product polymer, and a hydrophobic end group portion (iii) for providing selective hydrophobic properties to the polymer.

The portion (i) supplying the ethylenically unsaturated end group can be a residue derived from an α,β-ethylenically unsaturated monocarboxylic acid. Alternatively, portion (i) of the associative monomer can be a residue derived from an allyl ether or vinyl ether; a nonionic vinyl-substituted urethane monomer, such as disclosed in U.S. Reissue Pat. No. 33,156 or U.S. Pat. No. 5,294,692; or a vinyl-substituted urea reaction product, such as disclosed in U.S. Pat. No. 5,011,978; the relevant disclosures of each are incorporated herein by reference.

The mid-section portion (ii) is a polyoxyalkylene segment of about 2 to about 150 in one aspect, from about 10 to about 120 in another aspect, and from about 15 to about 60 in a further aspect of repeating $C_2$-$C_4$ alkylene oxide units. The mid-section portion (ii) includes polyoxyethylene, polyoxypropylene, and polyoxybutylene segments, and combinations thereof comprising from about 2 to about 150 in one aspect, from about 5 to about 120 in another aspect, and from about 10 to about 60 in a further aspect of ethylene, propylene and/or butylene oxide units, arranged in random or block sequences of ethylene oxide, propylene oxide and/or butylene oxide units.

The hydrophobic end group portion (iii) of the associative monomer is a hydrocarbon moiety belonging to one of the following hydrocarbon classes: a $C_8$-$C_{30}$ linear alkyl, a $C_8$-$C_{30}$ branched alkyl, a $C_8$-$C_{30}$ carbocyclic alkyl, a $C_2$-$C_{30}$ alkyl-substituted phenyl, an araalkyl substituted phenyl, and aryl-substituted $C_2$-$C_{30}$ alkyl groups.

Non-limiting examples of suitable hydrophobic end group portions (iii) of the associative monomers are linear or branched alkyl groups having about 8 to about 30 carbon atoms, such as capryl ($C_8$), iso-octyl (branched $C_8$), decyl ($C_{10}$), lauryl ($C_{12}$), myristyl ($C_{14}$), cetyl ($C_{16}$), cetearyl ($C_{16}$-$C_{18}$), stearyl ($C_{18}$), isostearyl (branched $C_{18}$), arachidyl ($C_{20}$), behenyl ($C_{22}$), lignoceryl ($C_{24}$), cerotyl ($C_{26}$), montanyl ($C_{28}$), melissyl ($C_{30}$), and the like.

Examples of linear and branched alkyl groups having about 8 to about 30 carbon atoms that are derived from a natural source include, without being limited thereto, alkyl groups derived from hydrogenated peanut oil, soybean oil and canola oil (all predominately $C_{18}$), hydrogenated tallow oil ($C_{16}$-$C_{18}$), and the like; and hydrogenated $C_{10}$-$C_{30}$ terpenols, such as hydrogenated geraniol (branched $C_{10}$), hydrogenated farnesol (branched $C_{15}$), hydrogenated phytol (branched $C_{20}$), and the like.

Non-limiting examples of suitable $C_2$-$C_{30}$ alkyl-substituted phenyl groups include octylphenyl, nonylphenyl, decylphenyl, dodecylphenyl, hexadecylphenyl, octadecylphenyl, isooctylphenyl, sec-butylphenyl, and the like.

Exemplary aryl-substituted $C_2$-$C_{40}$ alkyl groups include, without limitation thereto, styryl (e.g., 2-phenylethyl), distyryl (e.g., 2,4-diphenylbutyl), tristyryl (e.g., 2,4,6-triphenylhexyl), 4-phenylbutyl, 2-methyl-2-phenylethyl, tristyrylphenolyl, and the like.

Suitable $C_8$-$C_{30}$ carbocylic alkyl groups include, without being limited thereto, groups derived from sterols from animal sources, such as cholesterol, lanosterol, 7-dehydrocholesterol, and the like; from vegetable sources, such as phytosterol, stigmasterol, campesterol, and the like; and from yeast sources, such as ergosterol, mycosterol, and the like. Other carbocyclic alkyl hydrophobic end groups useful in the present invention include, without being limited thereto, cyclooctyl, cyclododecyl, adamantyl, decahydronaphthyl, and groups derived from natural carbocyclic materials, such as pinene, hydrogenated retinol, camphor, isobornyl alcohol, and the like.

Useful associative monomers can be prepared by any method known in the art. See, for example, U.S. Pat. No. 4,421,902 to Chang et al.; U.S. Pat. No. 4,384,096 to Sonnabend; U.S. Pat. No. 4,514,552 to Shay et al.; U.S. Pat. No. 4,600,761 to Ruffner et al.; U.S. Pat. No. 4,616,074 to Ruffner; U.S. Pat. No. 5,294,692 to Barron et al.; U.S. Pat. No. 5,292,843 to Jenkins et al.; U.S. Pat. No. 5,770,760 to Robinson; and U.S. Pat. No. 5,412,142 to Wilkerson, III et al.; the pertinent disclosures of which are incorporated herein by reference.

In one aspect, exemplary associative monomers include those represented by formulas (VII) and (VIIA) as follows:

VII

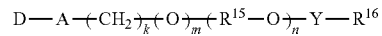

VIIA wherein $R^{14}$ is hydrogen or methyl; A is —$CH_2C(O)O$—, —$C(O)O$—, —$O$—, —$CH_2O$—, —$NHC(O)NH$—, —$C(O)NH$—, —$Ar$—$(CE_2)_z$—$NHC(O)O$—, —$Ar$—$(CE_2)_z$—$NHC(O)NH$—, or —$CH_2CH_2NHC(O)$—; Ar is a divalent arylene (e.g., phenylene); E is H or methyl; z is 0 or 1; k is an integer ranging from about 0 to about 30, and m is 0 or 1, with the proviso that when k is 0, m is 0, and when k is in the range of 1 to about 30, m is 1; D represents a vinyl or an allyl moiety; $(R^{15}$—$O)_n$ is a polyoxyalkylene moiety, which can be a homopolymer, a random copolymer, or a block copolymer of $C_2$-$C_4$ oxyalkylene units, $R^{15}$ is a divalent alkylene moiety selected from $C_2H_4$, $C_3H_6$, or $C_4H_8$, and combinations thereof; and n is an integer in the range of about 2 to about 150 in one aspect, from about 10 to about 120 in another aspect, and from about 15 to about 60 in a further aspect; Y is —$R^{15}O$—, —$R^{15}NH$—, —$C(O)$—, —$C(O)NH$—, —$R^{15}NHC(O)NH$—, or —$C(O)NHC(O)$—; $R^{16}$ is a substituted or unsubstituted alkyl selected from a $C_8$-$C_{30}$ linear alkyl, a $C_8$-$C_{30}$ branched alkyl, a $C_8$-$C_{30}$ carbocyclic alkyl, a $C_2$-$C_{30}$ alkyl-substituted phenyl, an araalkyl substituted phenyl, and an aryl-substituted $C_2$-$C_{30}$ alkyl; wherein the $R^{16}$ alkyl group, aryl group, phenyl group optionally comprises one or more substituents selected from the group consisting of a hydroxyl group, an alkoxyl group, benzyl group phenylethyl group, and a halogen group.

In one aspect, the hydrophobically modified associative monomer is an alkoxylated (meth)acrylate having a hydrophobic group containing 8 to 30 carbon atoms represented by the following formula:

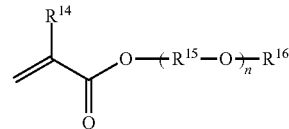

VIIB wherein $R^{14}$ is hydrogen or methyl; $R^{15}$ is a divalent alkylene moiety independently selected from $C_2H_4$, $C_3H_6$, and $C_4H_8$, and n represents an integer ranging from about 2 to about 150 in one aspect, from about 5 to about 120 in another aspect, and from about 10 to about 60 in a further aspect, ($R^{15}$—O) can be arranged in a random or a block configuration; $R^{16}$ is a substituted or unsubstituted alkyl selected from a $C_8$-$C_{30}$ linear alkyl, a $C_8$-$C_{30}$ branched alkyl, a $C_8$-$C_{30}$ carbocyclic alkyl, a $C_2$-$C_{30}$ alkyl-substituted phenyl, and an aryl-substituted $C_2$-$C_{30}$ alkyl.

Representative monomers under formula (VII) include lauryl polyethoxylated methacrylate (LEM), cetyl polyethoxylated methacrylate (OEM), cetearyl polyethoxylated methacrylate (CSEM), stearyl polyethoxylated (meth)acrylate, arachidyl polyethoxylated (meth)acrylate, behenyl polyethoxylated methacrylate (BEM), cerotyl polyethoxylated (meth)acrylate, montanyl polyethoxylated (meth)acrylate, melissyl polyethoxylated (meth)acrylate, phenyl polyethoxylated (meth)acrylate, nonylphenyl polyethoxylated (meth)acrylate, ω-tristyrylphenyl polyoxyethylene methacrylate, where the polyethoxylated portion of the monomer contains about 2 to about 150 ethylene oxide units in one aspect, from about 5 to about 120 in another aspect, and from about 10 to about 60 in a further aspect; octyloxy polyethyleneglycol (8) polypropyleneglycol (6) (meth)acrylate, phenoxy polyethylene glycol (6) polypropylene glycol (6) (meth)acrylate, and nonylphenoxy polyethylene glycol polypropylene glycol(meth)acrylate.

The semi-hydrophobic monomers of the invention are structurally similar to the associative monomer described above, but have a substantially non-hydrophobic end group portion. The semi-hydrophobic monomer has an ethylenically unsaturated end group portion (i) for addition polymerization with the other monomers of the invention; a polyoxyalkylene mid-section portion (ii) for imparting selective hydrophilic and/or hydrophobic properties to the product polymer and a semi-hydrophobic end group portion (iii). The unsaturated end group portion (i) supplying the vinyl or other ethylenically unsaturated end group for addition polymerization is preferably derived from an α,β-ethylenically unsaturated mono carboxylic acid. Alternatively, the end group portion (i) can be derived from an allyl ether residue, a vinyl ether residue or a residue of a nonionic urethane monomer.

The polyoxyalkylene mid-section (ii) specifically comprises a polyoxyalkylene segment, which is substantially similar to the polyoxyalkylene portion of the associative monomers described above. In one aspect, the polyoxyalkylene portions (ii) include polyoxyethylene, polyoxypropylene, and/or polyoxybutylene units comprising from about 2 to about 150 in one aspect, from about 5 to about 120 in another aspect, and from about 10 to about 60 in a further aspect of ethylene oxide, propylene oxide, and/or butylene oxide units, arranged in random or blocky sequences.

In one aspect, the semi-hydrophobic monomer can be represented by the following formulas:

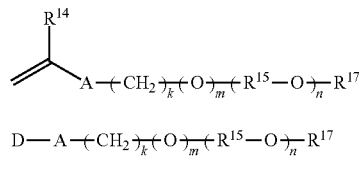

wherein $R^{14}$ is hydrogen or methyl; A is —$CH_2C(O)O$—, —$C(O)O$—, —O—, —$CH_2O$—, —NHC(O)NH—, —C(O)NH—, —Ar—$(CE_2)_z$—NHC(O)O—, —Ar—$(CE_2)_z$—NHC(O)NH—, or —$CH_2CH_2NHC(O)$—; Ar is a divalent arylene (e.g., phenylene); E is H or methyl; z is 0 or 1; k is an integer ranging from about 0 to about 30, and m is 0 or 1, with the proviso that when k is 0, m is 0, and when k is in the range of 1 to about 30, m is 1; ($R^{15}$—O)$_n$ is a polyoxyalkylene moiety, which can be a homopolymer, a random copolymer, or a block copolymer of $C_2$-$C_4$ oxyalkylene units, $R^{15}$ is a divalent alkylene moiety selected from $C_2H_4$, $C_3H_6$, or $C_4H_8$, and combinations thereof; and n is an integer in the range of about 2 to about 150 in one aspect, from about 5 to about 120 in another aspect, and from about 10 to about 60 in a further aspect; $R^{17}$ is selected from hydrogen and a linear or branched $C_1$-$C_4$ alkyl group (e.g., methyl, ethyl, propyl, iso-propyl, butyl, iso-butyl, and tert-butyl); and D represents a vinyl or an allyl moiety.

In one aspect, the semi-hydrophobic monomer under formula VIII can be represented by the following formulas:

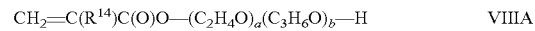

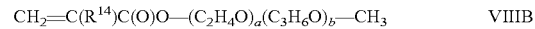

wherein $R^{14}$ is hydrogen or methyl, and "a" is an integer ranging from 0 or 2 to about 120 in one aspect, from about 5 to about 45 in another aspect, and from about 10 to about 0.25 in a further aspect, and "b" is an integer ranging from about 0 or 2 to about 120 in one aspect, from about 5 to about 45 in another aspect, and from about 10 to about 0.25 in a further aspect, subject to the proviso that "a" and "b" cannot be 0 at the same time.

Examples of semi-hydrophobic monomers under formula VIIIA include polyethyleneglycol methacrylate available under the product names Blemmer® PE-90 ($R^{14}$=methyl, a=2, b=0), PE-200 ($R^{14}$=methyl, a=4.5, b=0), and PE-350 ($R^{14}$=methyl a=8, b=0,); polypropylene glycol methacrylate available under the product names Blemmer® PP-1000 ($R^{14}$=methyl, b=4-6, a=0), PP-500 ($R^{14}$=methyl, a=0, b=9), PP-800 ($R^{14}$=methyl, a=0, b=13); polyethyleneglycol polypropylene glycol methacrylate available under the product names Blemmer® 50PEP-300 ($R^{14}$=methyl, a=3.5, b=2.5), 70PEP-350B ($R^{14}$=methyl, a=5, b=2); polyethyleneglycol acrylate available under the product names Blemmer® AE-90 ($R^{14}$=hydrogen, a=2, b=0), AE-200 ($R^{14}$=hydrogen, a=2, b=4.5), AE-400 ($R^{14}$=hydrogen, a=10, b=0); polypropyleneglycol acrylate available under the product names Blemmer® AP-150 ($R^{14}$=hydrogen, a=0, b=3), AP-400 ($R^{14}$=hydrogen, a=0, b=6), AP-550 ($R^{14}$=hydrogen, a=0, b=9). Blemmer® is a trademark of NOF Corporation, Tokyo, Japan.

Examples of semi-hydrophobic monomers under formula VIIIB include methoxypolyethyleneglycol methacrylate available under the product names Visiomer® MPEG 750 MA W ($R^{14}$=methyl, a=17, b=0), MPEG 1005 MA W ($R^{14}$=methyl, a=22, b=0), MPEG 2005 MA W ($R^{14}$=methyl, a=45, b=0), and MPEG 5005 MA W ($R^{14}$=methyl, a=113, b=0) from Evonik Röhm GmbH, Darmstadt, Germany); Bisomer® MPEG 350 MA ($R^{14}$=methyl, a=8, b=0), and MPEG 550 MA ($R^{14}$=methyl, a=12, b=0) from GEO Specialty Chemicals, Ambler Pa.; Blemmer® PME-100 ($R^{14}$=methyl, a=2, b=0), PME-200 ($R^{14}$=methyl, a=4, b=0), PME-400 ($R^{14}$=methyl, a=9, b=0), PME-1000 ($R^{14}$=methyl, a=23, b=0), PME-4000 ($R^{14}$=methyl, a=90, b=0).

In one aspect, the semi-hydrophobic monomer set forth in formula IX can be represented by the following formulas:

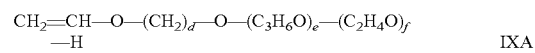

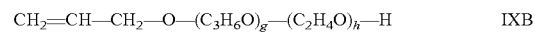

wherein d is an integer of 2, 3, or 4; e is an integer in the range of from about 1 to about 10 in one aspect, from about 2 to about 8 in another aspect, and from about 3 to about 7 in a further aspect; f is an integer in the range of from about 5 to about 50 in one aspect, from about 8 to about 40 in another aspect, and from about 10 to about 30 in a further aspect; g is an integer in the range of from 1 to about 10 in one aspect, from about 2 to about 8 in another aspect, and from about 3 to about 7 in a further aspect; and h is an integer in the range of from about 5 to about 50 in one aspect, and from about 8 to about 40 in another aspect; e, f, g, and h can be 0 subject to the proviso that e and f cannot be 0 at the same time, and g and h cannot be 0 at the same time.

Monomers under formulas IXA and IXB are commercially available under the trade names Emulsogen® R109, R208, R307, RAL109, RAL208, and RAL307 sold by Clariant Corporation; BX-AA-E5P5 sold by Bimax, Inc.; and combinations thereof. EMULSOGEN7 R109 is a randomly ethoxylated/propoxylated 1,4-butanediol vinyl ether having the empirical formula $CH_2=CH-O(CH_2)_4O(C_3H_6O)_4(C_2H_4O)_{10}H$; Emulsogen® R208 is a randomly ethoxylated/propoxylated 1,4-butanediol vinyl ether having the empirical formula $CH_2=CH-O(CH_2)_4O(C_3H_6O)_4(C_2H_4O)_{20}H$; Emulsogen® R307 is a randomly ethoxylated/propoxylated 1,4-butanediol vinyl ether having the empirical formula $CH_2=CH-O(CH_2)_4O(C_3H_6O)_4(C_2H_4O)_{30}H$; Emulsogen® RAL109 is a randomly ethoxylated/propoxylated allyl ether having the empirical formula $CH_2=CHCH_2O(C_3H_6O)_4(C_2H_4O)_{10}H$; Emulsogen® RAL208 is a randomly ethoxylated/propoxylated allyl ether having the empirical formula $CH_2=CHCH_2O(C_3H_6O)_4(C_2H_4O)_{20}H$; Emulsogen® RAL307 is a randomly ethoxylated/propoxylated allyl ether having the empirical formula $CH_2=CHCH_2O(C_3H_6O)_4(C_2H_4O)_{30}H$; and BX-AA-E5P5 is a randomly ethoxylated/propoxylated allyl ether having the empirical formula $CH_2=CHCH_2O(C_3H_6O)_5(C_2H_4O)_5H$.

In the associative and semi-hydrophobic monomers of the invention, the polyoxyalkylene mid-section portion contained in these monomers can be utilized to tailor the hydrophilicity and/or hydrophobicity of the polymers in which they are included. For example, mid-section portions rich in ethylene oxide moieties are more hydrophilic while mid-section portions rich in propylene oxide moieties are more hydrophobic. By adjusting the relative amounts of ethylene oxide to propylene oxide moieties present in these monomers the hydrophilic and hydrophobic properties of the polymers in which these monomers are included can be tailored as desired.

The amount of associative and/or semi-hydrophobic monomer utilized in the preparation of the polymers of the present invention can vary widely and depends, among other things, on the final rheological and aesthetic properties desired in the polymer. When utilized, the monomer reaction mixture contains one or more monomers selected from the associative and/or semi-hydrophobic monomers disclosed above in amounts ranging from about 0.01 to about 15 wt. % in one aspect, from about 0.1 wt. % to about 10 wt. % in another aspect, from about 0.5 to about 8 wt. % in still another aspect and from about 1, 2 or 3 to about 5 wt. % in a further aspect, based on the weight of the total monomers.

Ionizable Monomer

In one aspect of the invention, the nonionic, amphiphilic polymer compositions of the invention can be polymerized from a monomer composition including 0 to 5 wt. % of an ionizable and/or ionized monomer, based on the weight of the total monomers, so long as the irritation mitigation properties and the yield stress value of the surfactant compositions in which the polymers of the invention are included are not deleteriously affected.

In another aspect, the amphiphilic polymer compositions of the invention can be polymerized from a monomer composition comprising less than 3 wt. % in one aspect, less than 1 wt. % in a further aspect, less than 0.5 wt. % in a still further aspect, less than 0.1 wt. % in an additional aspect, and less than 0.05 wt. % in a further aspect, of an ionizable and/or an ionized moiety, based on the weight of the total monomers.

Ionizable monomers include monomers having a base neutralizable moiety and monomers having an acid neutralizable moiety. Base neutralizable monomers include olefinically unsaturated monocarboxylic and dicarboxylic acids and their salts containing 3 to 5 carbon atoms and anhydrides thereof. Examples include (meth)acrylic acid, itaconic acid, maleic acid, maleic anhydride, and combinations thereof. Other acidic monomers include styrenesulfonic acid, acrylamidomethylpropanesulfonic acid (AMPS® monomer), vinylsulfonic acid, vinylphosphonic acid, allylsulfonic acid, methallylsulfonic acid; and salts thereof.

Acid neutralizable monomers include olefinically unsaturated monomers which contain a basic nitrogen atom capable of forming a salt or a quaternized moiety upon the addition of an acid. For example, these monomers include vinylpyridine, vinylpiperidine, vinylimidazole, vinylmethylimidazole, dimethylaminomethyl(meth)acrylate, dimethylaminoethyl(meth)acrylate, diethylaminomethyl(meth)acrylate and methacrylate, dimethylaminoneopentyl(meth)acrylate, dimethylaminopropyl(meth)acrylate, and diethylaminoethyl(meth)acrylate.

Crosslinking Monomer

In one embodiment, the crosslinked, nonionic, amphiphilic polymers useful in the practice of the invention are polymerized from a monomer composition comprising a first monomer comprising at least one nonionic, hydrophilic unsaturated monomer, at least one nonionic, unsaturated hydrophobic monomer, and mixtures thereof, and a third monomer comprising at least one polyunsaturated crosslinking monomer. The crosslinking monomer(s) is utilized to polymerize covalent crosslinks into the polymer backbone. In one aspect, the crosslinking monomer is a polyunsaturated compound containing at least 2 unsaturated moieties. In another aspect, the crosslinking monomer contains at least 3 unsaturated moieties. Exemplary polyunsaturated compounds include di(meth)acrylate compounds such as ethylene glycol di(meth)acrylate, polyethylene glycol di(meth)acrylate, triethylene glycol di(meth)acrylate, 1,3-butylene glycol di(meth)acrylate, 1,6-butylene glycol di(meth)acrylate, 1,6-hexanediol di(meth)acrylate, neopentyl glycol di(meth)acrylate, 1,9-nonanediol di(meth)acrylate, 2,2'-bis(4-(acryloxy-propyloxyphenyl)propane, and 2,2'-bis(4-(acryloxydiethoxy-phenyl)propane; tri(meth)acrylate compounds such as, trimethylolpropane tri(meth)acrylate, trimethylolethane tri(meth)acrylate, and tetramethylolmethane tri(meth)acrylate; tetra(meth)acrylate compounds such as ditrimethylolpropane tetra(meth)acrylate, tetramethylolmethane tetra(meth)acrylate, and pentaerythritol tetra(meth)acrylate; hexa(meth)acrylate compounds such as dipentaerythritol hexa(meth)acrylate; allyl compounds such as allyl(meth)acrylate, diallylphthalate, diallyl itaconate, diallyl fumarate, and diallyl maleate; polyallyl ethers of sucrose having from 2 to 8 allyl groups per molecule, polyallyl ethers of pentaerythritol such as pentaerythritol diallyl ether, pentaerythritol triallyl ether, and pentaerythritol tetraallyl ether, and combinations thereof; polyallyl ethers of trimethylolpropane such as trimethylolpropane diallyl ether, trimethylolpropane triallyl ether, and combinations thereof. Other suitable polyunsaturated compounds include divinyl glycol, divinyl benzene, and methylenebisacrylamide.

In another aspect, suitable polyunsaturated monomers can be synthesized via an esterification reaction of a polyol made from ethylene oxide or propylene oxide or combinations thereof with unsaturated anhydride such as maleic anhydride, citraconic anhydride, itaconic anhydride, or an addition reaction with unsaturated isocyanate such as 3-isopropenyl-α-α-dimethylbenzene isocyanate.

Mixtures of two or more of the foregoing polyunsaturated compounds can also be utilized to crosslink the nonionic, amphiphilic polymers of the invention. In one aspect, the mixture of unsaturated crosslinking monomer contains an average of 2 unsaturated moieties. In another aspect, the mixture of crosslinking monomers contains an average of 2.5 unsaturated moieties. In still another aspect, the mixture of crosslinking monomers contains an average of about 3 unsaturated moieties. In a further aspect, the mixture of crosslinking monomers contains an average of about 3.5 unsaturated moieties.

In one embodiment of the invention, the crosslinking monomer component can be used in an amount ranging from about 0.01 to about 1 wt. % in one aspect, from about 0.05 to about 0.75 wt. % in another aspect, and from about 0.1 to about 0.5 wt. % in a further aspect, based on the dry weight of the nonionic, amphiphilic polymer of the invention.

In another embodiment of the invention, the crosslinking monomer component contains an average of about 3 unsaturated moieties and can be used in an amount ranging from about 0.01 to about 0.3 wt. % in one aspect, from about 0.02 to about 0.25 wt. % in another aspect, from about 0.05 to about 0.2 wt. % in a further aspect, and from about 0.075 to about 0.175 wt. % in a still further aspect, and from about 0.1 to about 0.15 wt. % in another aspect, based upon the total weight of the, nonionic, amphiphilic polymer of the invention.

In one aspect, the crosslinking monomer is selected from trimethylolpropane tri(meth)acrylate, trimethylolethane tri(meth)acrylate, tetramethylolmethane tri(meth)acrylate, pentaerythritol triallylether and polyallyl ethers of sucrose having 3 allyl groups per molecule.

Amphiphilic Polymer Synthesis

The linear and crosslinked, nonionic, amphiphilic, irritation mitigant polymers of the present invention can be made using conventional free-radical emulsion polymerization techniques. The polymerization processes are carried out in the absence of oxygen under an inert atmosphere such as nitrogen. The polymerization can be carried out in a suitable solvent system such as water. Minor amounts of a hydrocarbon solvent, organic solvent, as well as mixtures thereof can be employed. The polymerization reactions are initiated by any means which results in the generation of a suitable free-radical. Thermally derived radicals, in which the radical species is generated from thermal, homolytic dissociation of peroxides, hydroperoxides, persulfates, percarbonates, peroxyesters, hydrogen peroxide and azo compounds can be utilized. The initiators can be water soluble or water insoluble depending on the solvent system employed for the polymerization reaction.

The initiator compounds can be utilized in an amount of up to 30 wt. % in one aspect, 0.01 to 10 wt. % in another aspect, and 0.2 to 3 wt. % in a further aspect, based on the total weight of the dry polymer.

Exemplary free radical water soluble initiators include, but are not limited to, inorganic persulfate compounds, such as ammonium persulfate, potassium persulfate, and sodium persulfate; peroxides such as hydrogen peroxide, benzoyl peroxide, acetyl peroxide, and lauryl peroxide; organic hydroperoxides, such as cumene hydroperoxide and t-butyl hydroperoxide; organic peracids, such as peracetic acid, and water soluble azo compounds, such as 2,2'-azobis(tert-alkyl) compounds having a water solubilizing substituent on the alkyl group. Exemplary free radical oil soluble compounds include, but are not limited to 2,2'-azobisisobutyronitrile, and the like. The peroxides and peracids can optionally be activated with reducing agents, such as sodium bisulfite, sodium formaldehyde, or ascorbic acid, transition metals, hydrazine, and the like.

In one aspect, azo polymerization catalysts include the Vazo® free-radical polymerization initiators, available from DuPont, such as Vazo® 44 (2,2'-azobis(2-(4,5-dihydroimidazolyl)propane), Vazo® 56 (2,2'-azobis(2-methylpropionamidine)dihydrochloride), Vazo® 67 (2,2'-azobis(2-methylbutyronitrile)), and Vazo® 68 (4,4'-azobis(4-cyanovaleric acid)).

In emulsion polymerization processes, it can be advantageous to stabilize the monomer/polymer droplets or particles by means of surface active auxiliaries. Typically, these are emulsifiers or protective colloids. Emulsifiers used can be anionic, nonionic, cationic or amphoteric. Examples of anionic emulsifiers are alkylbenzenesulfonic acids, sulfonated fatty acids, sulfosuccinates, fatty alcohol sulfates, alkylphenol sulfates and fatty alcohol ether sulfates. Examples of usable nonionic emulsifiers are alkylphenol ethoxylates, primary alcohol ethoxylates, fatty acid ethoxylates, alkanolamide ethoxylates, fatty amine ethoxylates, EO/PO block copolymers and alkylpolyglucosides. Examples of cationic and amphoteric emulsifiers used are quaternized amine alkoxylates, alkylbetaines, alkylamidobetaines and sulfobetaines.

Optionally, the use of known redox initiator systems as polymerization initiators can be employed. Such redox initiator systems include an oxidant (intiator) and a reductant. Suitable oxidants include, for example, hydrogen peroxide, sodium peroxide, potassium peroxide, t-butyl hydroperoxide, t-amyl hydroperoxide, cumene hydroperoxide, sodium perborate, perphosphoric acid and salts thereof, potassium permanganate, and ammonium or alkali metal salts of peroxydisulfuric acid, typically at a level of 0.01% to 3.0% by weight, based on dry polymer weight, are used. Suitable reductants include, for example, alkali metal and ammonium salts of sulfur-containing acids, such as sodium sulfite, bisulfite, thiosulfate, hydrosulfite, sulfide, hydrosulfide or dithionite, formadinesulfinic acid, hydroxymethanesulfonic acid, acetone bisulfite, amines such as ethanolamine, glycolic acid, glyoxylic acid hydrate, ascorbic acid, isoascorbic acid, lactic acid, glyceric acid, malic acid, 2-hydroxy-2-sulfinatoacetic acid, tartaric acid and salts of the preceding acids typically at a level of 0.01% to 3.0% by weight, based on dry polymer weight, is used. In one aspect, combinations of peroxodisulfates with alkali metal or ammonium bisulfites can be used, for example, ammonium peroxodisulfate and ammonium bisulfite. In another aspect, combinations of hydrogen peroxide containing compounds (t-butyl hydroperoxide) as the oxidant with ascorbic or erythorbic acid as the reductant can be utilized. The ratio of peroxide-containing compound to reductant is within the range from 30:1 to 0.05:1.

Examples of suitable hydrocarbon solvents or diluents that can be utilized in the polymerization medium are aromatic solvents such as toluene, o-xylene, p-xylene, cumene, chlorobenzene, and ethylbenzene, aliphatic hydrocarbons, such as pentane, hexane, heptane, octane, nonane, decane, and the like, halogenated hydrocarbons, such as methylene chloride, alicyclic hydrocarbons, such as cyclopentane, methyl cyclopentane, cyclohexane, cycloheptane, cyclooctane, cyclononane, cyclodecane, and the like, and mixtures thereof. Suitable organic solvents include acetone, cyclohexanone, tetrahydrofuran, dioxane, glycols and glycol derivatives, polyalkylene glycols and derivatives thereof, diethyl ether, tert-butyl methyl ether, methyl acetate, ethyl acetate, propyl acetate, isopropyl acetate, butyl acetate, butyl propionate, and mixtures thereof. Mixtures of hydrocarbon solvents and organic solvents are also useful.

In the dispersion polymerization process, it can be advantageous to stabilize the monomer/polymer droplets or particles by means of surface active auxiliaries. Typically, these are emulsifiers, protective colloids or dispersion stabilizing polymers. The surface active auxiliaries used can be anionic, nonionic, cationic or amphoteric. Examples of anionic emulsifiers are alkylbenzenesulfonic acids, sulfonated fatty acids, sulfosuccinates, fatty alcohol sulfates, alkylphenol sulfates and fatty alcohol ether sulfates. Examples of usable nonionic emulsifiers are alkylphenol ethoxylates, primary alcohol ethoxylates, fatty acid ethoxylates, alkanolamide ethoxylates, fatty amine ethoxylates, EO/PO block copolymers and alkylpolyglucosides. Examples of cationic and amphoteric emulsifiers used are quaternized amine alkoxylates, alkylbetaines, alkylamidobetaines and sulfobetaines.

Examples of typical protective colloids are cellulose derivatives, polyethylene glycol, polypropylene glycol, copolymers of ethylene glycol and propylene glycol, polyvinyl acetate, poly(vinyl alcohol), partially hydrolyzed poly (vinyl alcohol), polyvinyl ether, starch and starch derivatives, dextran, polyvinylpyrrolidone, polyvinylpyridine, polyethyleneimine, polyvinylimidazole, polyvinylsuccinimide, polyvinyl-2-methylsuccinimide, polyvinyl-1,3-oxazolid-2-one, polyvinyl-2-methylimidazoline and maleic acid or anhydride copolymers. The emulsifiers or protective colloids are customarily used in concentrations from 0.05 to 20 wt. %, based on the weight of the total monomers.

The polymerization reaction can be carried out at temperatures ranging from 20 to 200° C. in one aspect, from 50 to 150° C. in another aspect, and from 60 to 100° C. in a further aspect.

The polymerization can be carried out the presence of chain transfer agents. Suitable chain transfer agents include, but are not limited to, thio- and disulfide containing compounds, such as $C_1$-$C_{18}$ alkyl mercaptans, such as tert-butyl mercaptan, n-octyl mercaptan, n-dodecyl mercaptan, tert-dodecyl mercaptan hexadecyl mercaptan, octadecyl mercaptan; mercaptoalcohols, such as 2-mercaptoethanol, 2-mercaptopropanol; mercaptocarboxylic acids, such as mercaptoacetic acid and 3-mercaptopropionic acid; mercaptocarboxylic acid esters, such as butyl thioglycolate, isooctyl thioglycolate, dodecyl thioglycolate, isooctyl 3-mercaptopropionate, and butyl 3-mercaptopropionate; thioesters; $C_1$-$C_{18}$ alkyl disulfides; aryldisulfides; polyfunctional thiols such as trimethylolpropane-tris-(3-mercaptopropionate), pentaerythritol-tetra-(3-mercaptopropionate), pentaerythritol-tetra-(thioglycolate), pentaerythritol-tetra-(thiolactate), dipentaerythritol-hexa-(thioglycolate), and the like; phosphites and hypophosphites; $C_1$-$C_4$ aldehydes, such as formaldehyde, acetaldehyde, propionaldehyde; haloalkyl compounds, such as carbon tetrachloride, bromotrichloromethane, and the like; hydroxylammonium salts such as hydroxylammonium sulfate; formic acid; sodium bisulfite; isopropanol; and catalytic chain transfer agents such as, for example, cobalt complexes (e.g., cobalt (II) chelates).

The chain transfer agents are generally used in amounts ranging from 0.1 to 10 wt. %, based on the total weight of the monomers present in the polymerization medium.

Dispersion Process

In another aspect of the invention, the crosslinked, nonionic, amphiphilic polymer is obtained by free-radical mediated dispersion polymerization in a non-aqueous medium that is a solvent for the monomers but a substantially non-solvent for the resulting polymers. Non-aqueous dispersion polymerization is discussed in detail in the book *Dispersion Polymerization in Organic Media*, edited by K. E. G. Barrett and published by John Wiley & Sons, New York, 1975. In a typical procedure for preparing a dispersion polymer, an organic solvent containing the polymerizable monomers, any polymerization additives such as processing aids, chelants, pH buffers and a stabilizer polymer is charged to an oxygen purged, temperature controlled reactor equipped with a mixer, a thermocouple, a nitrogen purging tube, and a reflux condenser. The reaction medium is mixed vigorously, heated to the desired temperature, and then a free-radical initiator is added. The polymerization is usually conducted at reflux temperature to prevent oxygen from inhibiting the reaction. Reflux temperature typically falls in the range of from about 40° C. to about 200° C. in one aspect, and from about 60° C. to about 140° C. in another aspect, depending on the boiling point of the solvents comprising the non-aqueous medium in which the polymer is prepared. The reaction medium is continually purged with nitrogen while maintaining temperature and mixing for several hours. After this time, the mixture is cooled to room temperature, and any post-polymerization additives are charged to the reactor. Hydrocarbons are preferably used as the dispersion solvent. The reaction time required in such a polymerization will vary with the reaction temperature employed, initiator system, and initiator level. Generally, this reaction time will vary from about 20 minutes up to about 30 hours. Commonly, it will be preferred to utilize a reaction time from about 1 up to about 6 hours.

Typically, polymerization of the monomers used to prepare the polymers is initiated by free-radical initiators that are soluble in the non-aqueous medium. Examples include azo compound initiators such as 2,2'-azobis(2,4-dimethylpentane nitrile), 2,2'-azobis(2-methylbutanenitrile), and 2,2'-azobis(2-methylbutyronitrile). The initiators can be used in customary amounts, for example 0.05 to 7 wt. %, based on the amount of monomers to be polymerized.

In one aspect, the solvent is a hydrocarbon selected from aliphatic and cycloaliphatic solvents, as well as mixtures thereof. Exemplary hydrocarbon solvents include pentane, hexane, heptane, octane, nonane, decane, cyclopentane, methyl cyclopentane, cyclohexane, cycloheptane, cyclooctane, cyclononane, cyclodecane, and their mixtures.

In another aspect, the solvent is an organic solvent selected from acetone, cyclohexanone, tetrahydrofuran, dioxane, glycols and glycol derivatives, polyalkylene glycols and derivatives thereof, diethyl ether, tert-butyl methyl ether, methyl acetate, methyl acetate, ethyl acetate, propyl acetate, isopropyl acetate, butyl acetate, butyl propionate, ethanol, isopropanol, water, and mixtures thereof.

The amount of solvent utilized normally will be in excess of the monomers to be polymerized and the proportion can vary from at least 1 wt. % of the monomer components and 99 wt. % solvent, up to about 65 wt. % polymerizable monomer components and 35 wt. % solvent. In another aspect, a concentration of about 10 to 60 wt. % polymerizable monomer components can be employed, where the weight percent is based on the total amount of monomer and solvent charged to the reaction vessel.

When mixtures of organic solvents and hydrocarbon solvents are utilized, the organic solvents and the hydrocarbon solvents can be premixed or can be added separately to the reaction mixture and the polymerization reaction can be carried out thereafter. The relative weight ratio of the at least one organic solvent to the at least one hydrocarbon solvent can be in the range of from about 95/5 to about 1/99 in one aspect, from about 80/20 to about 5/95 in another aspect, and from about 2:1 to 1:2 in a further aspect.

The stabilizer, typically a block or graft copolymer, prevents settling of the desired solid polymer product produced during the reaction. The block copolymer dispersion stabilizer can be selected from a variety of polymers containing at least two blocks wherein at least one of said blocks ("A" block) is soluble in the dispersion medium and at least another of said blocks ("B" block) is insoluble in the dispersion medium, and the stabilizer acts to disperse polymer products which are formed in the stabilizer's presence. The insoluble "B" block provides an anchor segment for attachment to the obtained polymer product, thus reducing the solubility of the polymerized product in the dispersion medium. The soluble "A" block of the dispersion stabilizer provides a sheath around the otherwise insoluble polymer and maintains the polymeric product as numerous small discrete particles rather than an agglomerated or highly coalesced mass. Details of the mechanism of such steric stabilization are described in Napper, D. H., "Polymeric Stabilization of Colloidal Dispersions," Academic Press, New York, N.Y., 1983. Representative stabilizers useful in the dispersion polymerization process of the invention are disclosed in U.S. Pat. Nos. 4,375,533; 4,419,502; 4,526,937; 4,692,502; 5,288,814; 5,349,030; 5,373,044; 5,468,797; and 6,538,067, which are incorporated herein by reference.

In one aspect of the invention, the steric stabilizer is selected from poly(12-hydroxystearic acid) such as disclosed in U.S. Pat. No. 5,288,814. In another aspect of the invention, the steric stabilizer comprises the ester of the reaction product of a $C_{18}$-$C_{24}$ hydrocarbyl substituted succinic acid or the anhydride thereof with a polyol such as disclosed in U.S. Pat. No. 7,044,988. In another aspect, the steric stabilizer comprises the ester of the reaction product of a $C_{20}$ to $C_{24}$ alkyl substituted succinic anhydride and a polyol selected from glycerin and/or a polyglycerol containing 2 to 6 glycerin units. U.S. Pat. Nos. 5,288,814 and 7,044,988 are herein incorporated by reference.

In still another aspect, the steric stabilizer is a copolymer of N-vinyl pyrrolidone/stearyl methacrylate/butyl acrylate. In one aspect the comonomers are incorporated into the stabilizer polymer in a weight ratio of 50/30/20, respectively. Mixtures of this steric stabilizer with esters and half esters of the reaction product of the $C_{12}$ to $C_{30}$ alkenyl substituted succinic anhydride and a polyol selected from $C_2$ to $C_4$ glycols are also contemplated.

The amount of steric stabilizer used in the polymerization process of this invention will cause variations in the size and specific surface area of the disperse polymer. In general, the amount of stabilizer utilized can range from 0.1 to 10 wt. % of the monomers present in the main polymerization process. Of course, smaller particles of disperse polymer require more stabilizer than large particles of disperse polymer.

In one aspect, the crosslinked, nonionic, amphiphilic polymers of the invention are selected from a dispersion polymer polymerized from a monomer mixture comprising 95 to 99.5 wt. % of a combination of at least one vinyl lactam and at least one vinyl ester of a $C_1$-$C_{22}$ carboxylic acid, wherein at least 60 wt. % of said monomer combination is selected from a vinyl lactam, 0.05 to 5 wt. % of at least one $C_8$-$C_{22}$ alkyl(meth)acrylate, optionally up to 5 wt. % of hydrophobically modified alkoxylated associative and/or a semi-hydrophobic monomer (said weight percent is based on the weight of the total monomers), and 0.01 to 1 wt. % of a crosslinking monomer (based on the weight of the dry polymer). When the optional associative and/or semi-hydrophobic monomer is present, the combined weight percentage of the $C_8$-$C_{22}$ alkyl(meth)acrylate and the associative and/or semi-hydrophobic monomer cannot exceed 5 wt. % of the weight of the total monomer composition.

In another embodiment, the crosslinked, nonionic, amphiphilic dispersion polymer is polymerized from a monomer mixture comprising 60 to 90 wt. % of N-vinyl pyrrolidone, 10 to 35 wt. % of at least one vinyl ester selected from vinyl acetate, vinyl propionate, vinyl butyrate, vinyl isobutyrate, vinyl valerate, vinyl hexanoate, vinyl 2-methylhexanate, vinyl 2-ethylhexanoate, vinyl iso-octanoate, vinyl nonanoate, vinyl neodecanoate, vinyl decanoate, vinyl versatate, vinyl laurate, vinyl palmitate, and vinyl stearate, 0 or 0.5 to 5 wt. % of an $C_8$-$C_{22}$ alkyl(meth)acrylate selected from octyl(meth)acrylate, 2-ethylhexyl(meth)acrylate, decyl(meth)acrylate, isodecyl(meth)acrylate, lauryl(meth)acrylate, tetradecyl(meth)acrylate, hexadecyl(meth)acrylate, stearyl(meth)acrylate, and behenyl(meth)acrylate, 0 or 0.5 to 4.5 wt. % of at least one associative monomer and/or semi-hydrophobic monomer (said weight percent is based on the weight of the total monomers), and 0.01 to 1 wt. % of a crosslinking monomer (based on the weight of the dry polymer). When the optional hydrophobically modified ethoxylated (meth)acrylate is present the combined weight percentage of the $C_8$-$C_{22}$ alkyl(meth)acrylate and the associative monomer and/or the semi-hydrophobic monomer cannot exceed 5 wt. % of the weight of the total monomer composition.

Detersive Compositions

Surprisingly, the present crosslinked, nonionic, amphiphilic, irritation mitigant polymers can be activated by a surfactant to provide a stable yield stress cleansing composition with desirable rheological and aesthetic properties and the ability to suspend particulate and insoluble materials in an aqueous medium for indefinite periods of time independent of pH. The yield stress value, elastic modulus and optical clarity are substantially independent of pH in the compositions in which the present polymers are included. The nonionic, amphiphilic, irritation mitigant polymers of the invention are useful in the pH range of from about 2 to about 14 in one aspect, from about 3 to 11 in another aspect, and from about 4 to about 9 in a further aspect. Unlike the pH responsive crosslinked polymers (acid or base sensitive) that require neutralization with an acid or a base to impart a desired rheological profile, the crosslinked, nonionic, amphiphilic polymers of the rheological profiles of the invention are substantially independent of pH. By substantially independent of pH is meant that the yield stress fluid within which the polymer of the invention is included imparts a desired rheological profile (e.g., a yield stress of at least 0.1 Pa in one aspect, at least at least 0.5 Pa in another aspect, at least 1 Pa in still another aspect, and at least 2 Pa in a further aspect) across a wide pH range (e.g., from about 2 to about 14) wherein the standard deviation in yield stress values across the pH range is less than 1 Pa in one aspect, less than 0.5 Pa in another aspect, and less than 0.25 Pa in a further aspect of the invention.

In one exemplary aspect of the invention, the cleansing compositions comprise: i) at least one nonionic, amphiphilic, irritation mitigant polymer of the invention; ii) at least one surfactant selected from at least one anionic surfactant, at least one amphoteric surfactant, at least one nonionic surfactant, and combinations thereof; and iii) water.

In another exemplary aspect of the invention, the cleansing compositions comprise: i) at least one crosslinked, nonionic, amphiphilic irritation mitigant polymer of the invention; ii) at least one anionic surfactant; and iii) water.

In another exemplary aspect of the invention, the cleansing compositions comprise: i) at least one crosslinked, nonionic, amphiphilic, irritation mitigant polymer of the invention; ii) at least one anionic surfactant and at least one amphoteric surfactant; and iii) water.

In another exemplary aspect of the invention, the cleansing compositions comprise: i) at least one crosslinked, nonionic, amphiphilic irritation mitigant polymer of the invention; ii) at least one anionic surfactant, iii) an optional nonionic surfactant; and iv) water.

In another exemplary aspect of the invention, the cleansing compositions comprise: i) at least one crosslinked, nonionic, amphiphilic irritation mitigant polymer of the invention; ii) at least one anionic surfactant, iii) an amphoteric surfactant; iv) an optional nonionic surfactant; and v) water.

In another exemplary aspect of the invention, the cleansing compositions comprise: i) at least one crosslinked, nonionic, amphiphilic irritation mitigant polymer of the invention; ii) at least one anionic ethoxylated surfactant; iii) an optional nonionic surfactant; and iv) water. In one aspect, the average degree of ethoxylation in the anionic ethoxylated surfactant can range from about 1 to about 3. In another aspect, the average degree of ethoxylation is about 2.

In another exemplary aspect of the invention, the cleansing compositions comprise: i) at least one crosslinked, nonionic, amphiphilic irritation mitigant polymer of the invention; ii) at least one anionic ethoxylated surfactant; iii) at least one amphoteric surfactant, iv) an optional nonionic surfactant; and iv) water. In one aspect, the average degree of ethoxylation in the anionic ethoxylated surfactant can range from about 1 to about 3. In another aspect, the average degree of ethoxylation is about 2.

In another exemplary aspect of the invention, the cleansing compositions comprise: i) at least one crosslinked, nonionic, amphiphilic irritation mitigant polymer of the invention; ii) at least one anionic non-ethoxylated surfactant; iii) at least one anionic ethoxylated surfactant; iv) an optional nonionic surfactant; and v) water. In one aspect, the average degree of ethoxylation in the anionic ethoxylated surfactant can range from about 1 to about 3. In another aspect, the average degree of ethoxylation is about 2.

In another exemplary aspect of the invention, the cleansing compositions comprise: i) at least one crosslinked, nonionic, amphiphilic irritation mitigant polymer of the invention; ii) at least one anionic non-ethoxylated surfactant; iii) at least one anionic ethoxylated surfactant; iv) at least one amphoteric surfactant; v) an optional nonionic surfactant; and vi) water. In one aspect, the average degree of ethoxylation in the anionic ethoxylated surfactant can range from about 1 to about 3. In another aspect, the average degree of ethoxylation is about 2.

Any amount of the nonionic, amphiphilic polymeric material can be utilized so long as the amount is effective to induce a reduction in irritation to the skin and/or eyes when included in a cleansing composition comprising at least one surfactant selected from anionic surfactants, amphoteric surfactants, nonionic surfactants, and combinations thereof. In one aspect, the amount of irritation mitigant polymer that can be incorporated into the surfactant containing cleansing compositions of the invention ranges from about 0.5 to about 5 wt. % polymer solids (100% active polymer) based on the weight of the total composition. In another aspect, the amount of polymer utilized in the formulation ranges from about 0.75 wt. % to about 3.5 wt. %. In still another aspect, the amount of amphiphilic polymer employed in the cleansing composition ranges from about 1 to about 3 wt. %. In a further aspect, the amount of polymer employed in the cleansing composition ranges from about 1.5 wt. % to about 2.75 wt. %. In a still further aspect, the amount of polymer utilized in the cleansing composition ranges from about 2 to about 2.5 wt. %.

In one aspect, the at least one nonionic, amphiphilic polymer utilized in formulating the mild cleansing compositions of the invention is a linear polymer. In one aspect, the number average molecular weight ($M_n$) of the linear copolymeric mitigants of the present invention as measured by gel permeation chromatography (GPC) calibrated with a poly (methyl methacrylate) (PMMA) standard is 500,000 daltons or less. In another aspect the molecular weight is 100,000 daltons or less. In still another aspect, the molecular weight ranges between about 5,000 and about 80,000 daltons, in a further aspect between about 10,000 and 50,000 daltons, and in a still further aspect between about 15,000 and 40,000 daltons In another aspect, the at least one nonionic, amphiphilic polymer utilized in formulating the mild cleansing compositions of the invention is crosslinked. The crosslinked nonionic, amphiphilic polymers of the invention are random copolymers and have weight average molecular weights ranging from above about 500,000 to at least about a billion Daltons or more in one aspect, and from about 600,000 to about 4.5 billion Daltons in another aspect, and from about 1,000,000 to about 3,000,000 Daltons in a further aspect, and from about 1,500,000 to about 2,000,000 Daltons in a still further aspect (see TDS-222, Oct. 15, 2007, Lubrizol Advanced Materials, Inc., which is herein incorporated by reference).

Detersive Surfactants

The surfactants utilized to formulate the mild cleansing compositions of the invention are from at least one detersive surfactant selected from anionic surfactants, amphoteric surfactants, nonionic surfactants, and mixtures thereof.

Non-limiting examples of anionic surfactants are disclosed in *McCutcheon's Detergents and Emulsifiers*, North American Edition, 1998, published by Allured Publishing Corporation; and McCutcheon's, *Functional Materials*, North American Edition (1992); both of which are incorporated by reference herein in their entirety. The anionic surfactant can be any of the anionic surfactants known or previously used in the art of aqueous surfactant compositions. Suitable anionic surfactants include but are not limited to alkyl sulfates, alkyl ether sulfates, alkyl sulphonates, alkaryl sulfonates, α-olefin-sulphonates, alkylamide sulphonates, alkarylpolyether sulphates, alkylamidoether sulphates, alkyl monoglyceryl ether sulfates, alkyl monoglyceride sulfates, alkyl monoglyceride sulfonates, alkyl succinates, alkyl sulfosuccinates, alkyl sulfosuccinamates, alkyl ether sulphosuccinates, alkyl amidosulfosuccinates; alkyl sulphoacetates, alkyl phosphates, alkyl ether phosphates, alkyl ether carboxylates, alkyl amidoethercarboxylates, N-alkylamino acids, N-acyl amino acids, alkyl peptides, N-acyl taurates, alkyl isethionates, carboxylate salts wherein the acyl group is derived from fatty acids; and the alkali metal, alkaline earth metal, ammonium, amine, and triethanolamine salts thereof.

In one aspect, the cation moiety of the forgoing salts is selected from sodium, potassium, magnesium, ammonium, mono-, di- and triethanolamine salts, and mono-, di-, and tri-isopropylamine salts. The alkyl and acyl groups of the foregoing surfactants contain from about 6 to about 24 carbon atoms in one aspect, from 8 to 22 carbon atoms in another aspect and from about 12 to 18 carbon atoms in a further aspect and can be saturated or unsaturated. The aryl groups in the surfactants are selected from phenyl or benzyl. The ether containing surfactants set forth above can contain from 1 to 10 ethylene oxide and/or propylene oxide units per surfactant molecule in one aspect, and from 1 to 3 ethylene oxide units per surfactant molecule in another aspect.

Examples of suitable anionic surfactants include but are not limited to the sodium, potassium, lithium, magnesium, and ammonium salts of laureth sulfate, trideceth sulfate, myreth sulfate, $C_{12}$-$C_{13}$ pareth sulfate, $C_{12}$-$C_{14}$ pareth sulfate, and $C_{12}$-$C_{15}$ pareth sulfate, ethoxylated with 1, 2, 3, 4 or 5 moles of ethylene oxide; sodium, potassium, lithium, magnesium, ammonium, and triethanolamine lauryl sulfate, coco sulfate, tridecyl sulfate, myrstyl sulfate, cetyl sulfate, cetearyl sulfate, stearyl sulfate, oleyl sulfate, and tallow sulfate, disodium lauryl sulfosuccinate, disodium laureth sulfosuccinate, sodium cocoyl isethionate, sodium $C_{12}$-$C_{14}$ olefin sulfonate, sodium laureth-6 carboxylate, sodium methyl cocoyl taurate, sodium cocoyl glycinate, sodium myristyl sarcocinate, sodium dodecylbenzene sulfonate, sodium cocoyl sarcosinate, sodium cocoyl glutamate, potassium myristoyl glutamate, triethanolamine monolauryl phosphate, and fatty acid soaps, including the sodium, potassium, ammonium, and triethanolamine salts of a saturated and unsaturated fatty acids containing from about 8 to about 22 carbon atoms.

The term "amphoteric surfactant" as used herein, is also intended to encompass zwitterionic surfactants, which are well known to formulators skilled in the art as a subset of amphoteric surfactants. Nonlimiting examples of amphoteric surfactants are disclosed *McCutcheon's Detergents and Emulsifiers*, North American Edition, supra, and *McCutcheon's, Functional Materials*, North American Edition, supra; both of which are incorporated by reference herein in their entirety. Suitable examples include but are not limited to amino acids (e.g., N-alkyl amino acids and N-acyl amino acids), betaines, sultaines, and alkyl amphocarboxylates.

Amino acid based surfactants suitable in the practice of the present invention include surfactants represented by the formula:

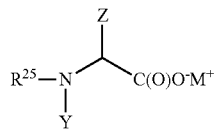

wherein $R^{25}$ represents a saturated or unsaturated hydrocarbon group having 10 to 22 carbon atoms or an acyl group containing a saturated or unsaturated hydrocarbon group having 9 to 22 carbon atoms, Y is hydrogen or methyl, Z is selected from hydrogen, —$CH_3$, —$CH(CH_3)_2$, —$CH_2CH(CH_3)_2$, —$CH(CH_3)CH_2CH_3$, —$CH_2C_6H_5$, —$CH_2C_6H_4OH$, —$CH_2OH$, —$CH(OH)CH_3$, —$(CH_2)_4$ $NH_2$, —$(CH_2)_3NHC(NH)NH_2$, —$CH_2C(O)O^-M^+$, —$(CH_2)_2C(O)O^-M^+$. M is a salt forming cation. In one aspect, $R^{25}$ represents a radical selected from a linear or branched $C_{10}$ to $C_{22}$ alkyl group, a linear or branched $C_{10}$ to $C_{22}$ alkenyl group, an acyl group represented by $R^{26}C(O)$—, wherein $R^{26}$ is selected from a linear or branched $C_9$ to $C_{22}$ alkyl group, a linear or branched $C_9$ to $C_{22}$ alkenyl group. In one aspect, $M^+$ is a cation selected from sodium, potassium, ammonium, and triethanolamine (TEA).

The amino acid surfactants can be derived from the alkylation and acylation of α-amino acids such as, for example, alanine, arginine, aspartic acid, glutamic acid, glycine, isoleucine, leucine, lysine, phenylalanine, serine, tyrosine, and valine. Representative N-acyl amino acid surfactants are, but not limited to the mono- and di-carboxylate salts (e.g., sodium, potassium, ammonium and TEA) of N-acylated glutamic acid, for example, sodium cocoyl glutamate, sodium lauroyl glutamate, sodium myristoyl glutamate, sodium palmitoyl glutamate, sodium stearoyl glutamate, disodium cocoyl glutamate, disodium stearoyl glutamate, potassium cocoyl glutamate, potassium lauroyl glutamate, and potassium myristoyl glutamate; the carboxylate salts (e.g., sodium, potassium, ammonium and TEA) of N-acylated alanine, for example, sodium cocoyl alaninate, and TEA lauroyl alaninate; the carboxylate salts (e.g., sodium, potassium, ammonium and TEA) of N-acylated glycine, for example, sodium cocoyl glycinate, and potassium cocoyl glycinate; the carboxylate salts (e.g., sodium, potassium, ammonium and TEA) of N-acylated sarcosine, for example, sodium lauroyl sarcosinate, sodium cocoyl sarcosinate, sodium myristoyl sarcosinate, sodium oleoyl sarcosinate, and ammonium lauroyl sarcosinate; and mixtures of the foregoing surfactants.

The betaines and sultaines useful in the present invention are selected from alkyl betaines, alkylamino betaines, and alkylamido betaines, as well as the corresponding sulfobetaines (sultaines) represented by the formulas:

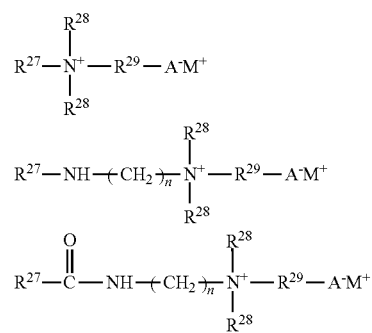

wherein $R^{27}$ is a $C_7$-$C_{22}$ alkyl or alkenyl group, each $R^{28}$ independently is a $C_1$-$C_4$ alkyl group, $R^{29}$ is a $C_1$-$C_5$ alkylene group or a hydroxy substituted $C_1$-$C_5$ alkylene group, n is an integer from 2 to 6, A is a carboxylate or sulfonate group, and M is a salt forming cation. In one aspect, $R^{27}$ is a $C_{11}$-$C_{18}$ alkyl group or a $C_{11}$-$C_{18}$ alkenyl group. In one aspect, $R^{28}$ is methyl. In one aspect, $R^{29}$ is methylene, ethylene or hydroxy propylene. In one aspect, n is 3. In a further aspect, M is selected from sodium, potassium, magnesium, ammonium, and mono-, di- and triethanolamine cations.

Examples of suitable betaines include, but are not limited to, lauryl betaine, coco betaine, oleyl betaine, cocohexadecyl dimethylbetaine, lauryl amidopropyl betaine, cocoamidopropyl betaine (CAPB), and cocamidopropyl hydroxysultaine.

The alkylamphocarboxylates such as the alkylamphoacetates and alkylamphopropionates (mono- and disubstituted carboxylates) can be represented by the formula:

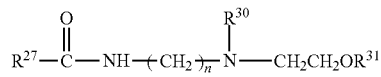

wherein $R^{27}$ is a $C_7$-$C_{22}$ alkyl or alkenyl group, $R^{30}$ is —$CH_2C(O)O^-M^+$, —$CH_2CH_2C(O)O^-M^+$, or —$CH_2CH(OH)CH_2SO_3^-M^+$, $R^{31}$ is hydrogen or —$CH_2C(O)O^-M^+$, and M is a cation selected from sodium, potassium, magnesium, ammonium, and mono-, di- and triethanolamine.

Exemplary alkylamphocarboxylates include, but are not limited to, sodium cocoamphoacetate, sodium lauroamphoacetate, sodium capryloamphoacetate, disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, and disodium capryloamphodipropionate.

Non-limiting examples of nonionic surfactants are disclosed in *McCutcheon's Detergents and Emulsifiers*, North American Edition, 1998, supra; and McCutcheon's, *Functional Materials*, North American, supra; both of which are incorporated by reference herein in their entirety. Additional Examples of nonionic surfactants are described in U.S. Pat. No. 4,285,841, to Barrat et al., and U.S. Pat. No. 4,284,532, to Leikhim et al., both of which are incorporated by reference herein in their entirety. Nonionic surfactants typically have a hydrophobic portion, such as a long chain alkyl group or an alkylated aryl group, and a hydrophilic portion containing various degrees of ethoxylation and/or propoxylation (e.g., 1 to about 50) ethoxy and/or propoxy moieties. Examples of some classes of nonionic surfactants that can be used include, but are not limited to, ethoxylated alkylphenols, ethoxylated and propoxylated fatty alcohols, polyethylene glycol ethers of methyl glucose, polyethylene glycol ethers of sorbitol, ethylene oxide-propylene oxide block copolymers, ethoxylated esters of fatty acids, condensation products of ethylene oxide with long chain amines or amides, condensation products of ethylene oxide with alcohols, and mixtures thereof.

Suitable nonionic surfactants include, for example, alkyl polysaccharides, alcohol ethoxylates, block copolymers, castor oil ethoxylates, ceto/oleyl alcohol ethoxylates, cetearyl alcohol ethoxylates, decyl alcohol ethoxylates, dinonyl phenol ethoxylates, dodecyl phenol ethoxylates, end-capped ethoxylates, ether amine derivatives, ethoxylated alkanolamides, ethylene glycol esters, fatty acid alkanolamides, fatty alcohol alkoxylates, lauryl alcohol ethoxylates, monobranched alcohol ethoxylates, nonyl phenol ethoxylates, octyl phenol ethoxylates, oleyl amine ethoxylates, random copolymer alkoxylates, sorbitan ester ethoxylates, stearic acid ethoxylates, stearyl amine ethoxylates, tallow oil fatty acid ethoxylates, tallow amine ethoxylates, tridecanol ethoxylates, acetylenic diols, polyoxyethylene sorbitols, and mixtures thereof. Various specific examples of suitable nonionic surfactants include, but are not limited to, methyl gluceth-10, PEG-20 methyl glucose distearate, PEG-20 methyl glucose sesquistearate, ceteth-8, ceteth-12, dodoxynol-12, laureth-15, PEG-20 castor oil, polysorbate 20, steareth-20, polyoxyethylene-10 cetyl ether, polyoxyethylene-10 stearyl ether, polyoxyethylene-20 cetyl ether, polyoxyethylene-10 oleyl ether, polyoxyethylene-20 oleyl ether, an ethoxylated nonylphenol, ethoxylated octylphenol, ethoxylated dodecylphenol, or ethoxylated fatty ($C_6$-$C_{22}$) alcohol, including 3 to 20 ethylene oxide moieties, polyoxyethylene-20 isohexadecyl ether, polyoxyethylene-23 glycerol laurate, polyoxyethylene-20 glyceryl stearate, PPG-10 methyl glucose ether, PPG-20 methyl glucose ether, polyoxyethylene-20 sorbitan monoesters, polyoxyethylene-80 castor oil, polyoxyethylene-15 tridecyl ether, polyoxyethylene-6 tridecyl ether, laureth-2, laureth-3, laureth-4, PEG-3 castor oil, PEG 600 dioleate, PEG 400 dioleate, poloxamers such as poloxamer 188, polysorbate 21, polysorbate 40, polysorbate 60, polysorbate 61, polysorbate 65, polysorbate 80, polysorbate 81, polysorbate 85, sorbitan caprylate, sorbitan cocoate, sorbitan diisostearate, sorbitan dioleate, sorbitan distearate, sorbitan fatty acid ester, sorbitan isostearate, sorbitan laurate, sorbitan oleate, sorbitan palmitate, sorbitan sesquiisostearate, sorbitan sesquioleate, sorbitan sesquistearate, sorbitan stearate, sorbitan triisostearate, sorbitan trioleate, sorbitan tristearate, sorbitan undecylenate, or mixtures thereof.

Alkyl glycoside nonionic surfactants can also be employed and are generally prepared by reacting a monosaccharide, or a compound hydrolyzable to a monosaccharide, with an alcohol such as a fatty alcohol in an acid medium. For example, U.S. Pat. Nos. 5,527,892 and 5,770,543 describe alkyl glycosides and/or methods for their preparation. Suitable examples are commercially available under the names of Glucopon™ 220, 225, 425, 600 and 625, PLANTACARE®, and PLANTAPON®, all of which are available from Cognis Corporation of Ambler, Pa.

In another aspect, nonionic surfactants include, but are not limited to, alkoxylated methyl glucosides such as, for example, methyl gluceth-10, methyl gluceth-20, PPG-10 methyl glucose ether, and PPG-20 methyl glucose ether, available from Lubrizol Advanced Materials, Inc., under the trade names, Glucam® E10, Glucam® E20, Glucam® P10, and Glucam® P20, respectively; and hydrophobically modified alkoxylated methyl glucosides, such as PEG 120 methyl glucose dioleate, PEG-120 methyl glucose trioleate, and PEG-20 methyl glucose sesquistearate, available from Lubrizol Advanced Materials, Inc., under the trade names, Glucamate® DOE-120, Glucamate™ LT, and Glucamate™ SSE-20, respectively, are also suitable. Other exemplary hydrophobically modified alkoxylated methyl glucosides are disclosed in U.S. Pat. Nos. 6,573,375 and 6,727,357, the disclosures of which are hereby incorporated by reference in their entirety.

Other useful nonionic surfactants include water soluble silicones such as PEG-10 Dimethicone, PEG-12 Dimethicone, PEG-14 Dimethicone, PEG-17 Dimethicone, PPG-12 Dimethicone, PPG-17 Dimethicone and derivatized/functionalized forms thereof such as Bis-PEG/PPG-20/20 Dimethicone Bis-PEG/PPG-16/16 PEG/PPG-16/16 Dimethicone, PEG/PPG-14/4 Dimethicone, PEG/PPG-20/20 Dimethicone, PEG/PPG-20/23 Dimethicone, and Perfluorononylethyl Carboxydecyl PEG-10 Dimethicone.

The amount of the at least one surfactant (active weight basis) utilized in formulating the cleansing compositions of the invention ranges from about 1 to about 30 wt. % based on the weight of the total composition. In another aspect, the amount of the at least one surfactant utilized in the formulation of the cleansing composition ranges from about 3 to about 25 wt. %. In still another aspect, the amount of the at least one surfactant employed in the cleansing composition ranges from about 5 to about 22 wt. %. In a further aspect, the amount of the at least one surfactant utilized ranges from about 6 to about 20 wt. %. In still a further aspect, the amount of at least one surfactant is about 10, 12, 14, 16, and 18 wt. % based on the total weight yield of the cleansing composition.

In one embodiment of the invention, the weight ratio (based on active material) of anionic surfactant (non-ethoxylated and/or ethoxylated) to amphoteric surfactant can range from about 10:1 to about 2:1 in one aspect, and can be 9:1, 8:1, 7:1 6:1, 5:1, 4.5:1, 4:1, or 3:1 in another aspect. When employing an ethoxylated anionic surfactant in combination with a non-ethoxylated anionic surfactant and an amphoteric surfactant, the weight ratio (based on active material) of ethoxylated anionic surfactant to non-ethoxylated anionic surfactant to amphoteric surfactant can range from about 3.5:3.5:1 in one aspect to about 1:1:1 in another aspect.

In one embodiment, the yield stress value of the cleansing composition containing the linear, nonionic, amphiphilic polymers of the invention is 0 Pa.

In one embodiment, the yield stress value of the cleansing composition containing the crosslinked nonionic, amphiphilic polymers of the invention is at least about 0.1 Pa in one aspect, about 0.5 Pa in one aspect, at least about 1 Pa in another aspect and at least about 1.5 Pa in a further aspect. In another embodiment, the yield stress of the cleansing composition ranges from about 0.1 to about 20 Pa in one aspect, from about 0.5 Pa to about 10 Pa in another aspect, from about 1 to about 3 Pa in a further aspect, and from about 1.5 to about 3.5 in a still further aspect.

Optionally, the cleansing compositions of the invention can contain an electrolyte. Suitable electrolytes are known compounds and include salts of multivalent anions, such as potassium pyrophosphate, potassium tripolyphosphate, and sodium or potassium citrate, salts of multivalent cations, including alkaline earth metal salts such as calcium chloride and calcium bromide, as well as zinc halides, barium chloride and calcium nitrate, salts of monovalent cations with monovalent anions, including alkali metal or ammonium halides, such as potassium chloride, sodium chloride, potassium iodide, sodium bromide, and ammonium bromide, alkali metal or ammonium nitrates, and blends thereof. The amount of the electrolyte used will generally depend on the amount of the amphiphilic polymer incorporated, but may be used at concentration levels of from about 0.1 to about 4 wt. % in one aspect and from about 0.2 to about 2 wt. % in another aspect, based on the weight of the total composition.

The cleansing composition must be easily pourable with a shear thinning index of less than 0.5 at shear rates between 0.1 and 1 reciprocal second. The cleansing compositions of the invention can be utilized in combination with an auxiliary rheology modifier (thickener) to enhance the yield value of a thickened liquid. In one aspect, the yield stress fluid of the invention can be combined with a nonionic rheology modifier which rheology modifier when utilized alone does not have a sufficient yield stress value. In one aspect, a rheology modifier can be combined with a nonionic rheology modifier to attain a desired yield stress value when a linear irritation mitigation polymer is utilized. Any rheology modifier is suitable including, but are not limited to, natural gums (e.g., polygalactomannan gums selected from fenugreek, cassia, locust bean, tara and guar), modified cellulose (e.g., ethylhexylethylcellulose (EHEC), hydroxybutylmethylcellulose (HBMC), hydroxyethylmethylcellulose (NEMC), hydroxypropylmethylcellulose (HPMC), methyl cellulose (MC), hydroxyethylcellulose (HEC), hydroxypropylcellulose (HPC) and cetyl hydroxyethylcellulose); and mixtures thereofmethylcellulose, polyethylene glycols (e.g., PEG 4000, PEG 6000, PEG 8000, PEG 10000, PEG 20000), polyvinyl alcohol, polyacrylamides (homopolymers and copolymers), and hydrophobically modified ethoxylated urethanes (HEUR). The rheology modifier can be utilized in an amount ranging from about 0.5 to about 25 wt. % in one aspect, from about 1 to about 15 wt. % in another aspect, and from about 2 to about 10 wt. % in a further aspect, and from about 2.5 to about 5 wt. % based on the weight of the total weight of the composition.

The linear and crosslinked, nonionic, amphiphilic polymers of the invention can be used in any cleansing or detersive application to mitigate irritation induced by harsh surfactants to the skin and/or eyes. The linear polymers of the invention can be utilized in detersive formulations where irritation mitigation is desirable but an increase in yield value or thickening is not. The crosslinked, nonionic, amphiphilic polymers of the invention can be used in any cleansing or detersive application to mitigate irritation induced by harsh surfactants to the skin and/or the eyes and requires a concomitant enhancement of yield stress properties.

In one embodiment, crosslinked, nonionic, amphiphilic polymers of the invention can be utilized to mitigate irritation to the skin and/or the eyes as well as to stably suspend particulate materials and insoluble droplets within a surfactant containing cleansing and cleaning composition formulated for the personal care and home care industries.

In the personal care industry, the crosslinked, nonionic, amphiphilic polymers of the invention can be utilized to improve mildness and the yield stress properties of cleansing compositions for the hair and skin, and can be utilized for the stable suspension of insoluble silicones, opacifiers and pearlescent agents (e.g., mica, coated mica, ethylene glycol monostearate (EGMS), ethylene glycol distearate (EGDS), polyethylene glycol monostearate (PGMS) or polyethyleneglycol distearate (PGDS)), pigments, exfoliants, antidandruff agents, clay, swellable clay, laponite, gas bubbles, liposomes, microsponges, cosmetic beads, cosmetic microcapsules, and flakes. These compositions may be in the form of a body wash, shower gel, bubble bath, two-in-one shampoo, conditioner, facial scrub, moisture rinse, make-up removal product, and the like.

Exemplary bead components include, but are not limited to, agar beads, alginate beads, jojoba beads, gelatin beads, Styrofoam™ beads, polyacrylate, polymethylmethacrylate (PMMA), polyethylene beads, Unispheres™ and Unipearls™ cosmetic beads (Induchem USA, Inc., New York, N.Y.), Lipocapsule™, Liposphere™, and Lipopearl™ microcapsules (Lipo Technologies Inc., Vandalia, Ohio), and Confetti II™ dermal delivery flakes (United-Guardian, Inc., Hauppauge, N.Y.). Beads can be utilized as aesthetic materials or can be used to encapsulate benefit agents to protect them from the deteriorating effects of the environment or for optimal delivery, release and performance in the final product.

In one aspect, the cosmetic beads range in size from about 0.5 to about 1.5 mm. In another aspect, the difference in specific gravity of the bead and water is between about +/−0.01 and 0.5 in one aspect and from about +/−0.2 to 0.3 g/ml in another aspect.

In one aspect, the microcapsules range in size from about 0.5 to about 300 μm. In another aspect, the difference in specific gravity between the microcapsules and water is from about +/−0.01 to 0.5. Non-limiting examples of microcapsule beads are disclosed in U.S. Pat. No. 7,786,027, the disclosure of which is herein incorporated by reference.

In one aspect of the invention, the amount of particulate component and/or insoluble droplets can range from about 0.1% to about 10% by weight based on the total weight of the composition.

The stable compositions maintain a smooth, acceptable rheology with good shear thinning properties without significant increases or decreases in viscosity, with no phase separation, e.g., settling or creaming out (rising to the surface), or loss of clarity over extended periods of time, such as for at least one month at 45° C.

In the home care industry, the crosslinked, nonionic, amphiphilic polymers of the invention can be utilized to improve mildness and the yield stress properties of detersive compositions for hard surfaces (e.g., floors, countertops, walls, wood surfaces, appliances, tile, and the like), fabric care, dish care, for improvement of cling (toilet bowl, sink and vertical surface cleaners) and for the stable suspension of abrasive materials in abrasive cleaners.

While overlapping weight ranges for the various components and ingredients that can be contained in the yield stress fluids of the invention have been expressed for selected embodiments and aspects of the invention, it should be readily apparent that the specific amount of each component in the compositions will be selected from its disclosed range such that the amount of each component is adjusted so that the sum of all components in the composition will total 100 weight percent. The amounts employed will vary with the purpose and character of the desired product and can be readily determined by one skilled in the formulation art and from the literature.

This invention is illustrated by the following examples that are merely for the purpose of illustration and are not to be regarded as limiting the scope of the invention or the manner in which it can be practiced. Unless specifically indicated otherwise, parts and percentages are given by weight.

The following abbreviations and trade names are utilized in the examples.

| Abbreviations and Trade Names | |
| --- | --- |
| APE | Allyl Pentaerythritol |
| n-BA | n-Butyl Acrylate |
| BEM | Ethoxylated Behenyl Methacrylate, Sipomer BEM, Rhodia |
| Chembetaine ™ CAD | Cocamidopropyl Betaine (amphoteric surfactant), Lubrizol Advanced Materials, Inc. (35% active) |
| CYCLO | Cyclohexane |
| LMA | Lauryl Methacrylate |
| SMA | Stearyl Methacrylate |
| Sulfochem ™ ES-2 | Sodium Laureth Sulfate - 2 moles of ethoxylation (anionic surfactant), Lubrizol Advanced Materials, Inc. (26% active) |
| VA | Vinyl Acetate |
| VA-10 | Vinyl Decanoate |
| VP | N-Vinylpyrrolidone |

Examples 1 to 4

A free radical initiated dispersion polymerization is utilized to make crosslinked, nonionic, amphiphilic polymers of the invention. The polymerization reactor consists of a water-cooled resin kettle equipped with a reflux condenser, nitrogen purging tube, a mechanical agitator and a thermalcouple connected to a temperature control module. Admixtures of monomers, cross-linkers and processing aids are set forth in Table 1 are first added to the resin kettle, followed by polymerization solvent. The quantities of these components in grams for the various polymer preparations are shown in the table. While the reaction medium is heated to the target polymerization temperature, the reactor is purged with nitrogen for at least half an hour. As the reactor temperature reaches the set polymerization temperature, typically at about 67° C., the initiator solution is injected to start the polymerization. The polymerization is continued for at least 6 hours at 67° C. before a series of shots of additional initiator solution are injected into the reactor to reduce residual monomers to acceptable levels. The final product is recovered as a fine powder after the polymerization solvent is removed by rotary evaporator under vacuum followed by a gentle milling process. The total polymer solids in the final dispersion is typically at about 30 wt. %.

TABLE 1

| Example No. | NVP (wt. %)[1] | VA (wt. %)[1] | SMA (wt. %)[1] | LMA (wt. %)[1] | VA-10 (wt. %)[1] | APE (wt. %)[2] | Stabilizer[3] (wt. %)[2] | PGS[4] (wt. %)[2] | CYCLO (wt. %)[2] | Initiator[5] (wt. %)[2] |
| --- | --- | --- | --- | --- | --- | --- | --- | --- | --- | --- |
| 1 | 84 | 15 | 1 | — | — | 0.1 | 6 | 1 | 231 | 0.12 |
| 2 | 84 | 15 | — | 1 | — | 0.1 | 6 | 1 | 231 | 0.12 |
| 3 | 64 | 35 | — | — | 1 | 0.1 | 6 | 1 | 230 | 0.12 |
| 4 | 84 | 15 | — | — | 1 | — | 6 | 1 | 231 | 0.12 |

[1]Based on the weight of the total monomers
[2]Based on the weight of the dry polymer
[3]50/30/20 (wt. %) copolymer of N-vinyl pyrrolidone/stearyl methacrylate/butyl methacrylate utilized as a dispersion polymerization stabilizer
[4]Reaction product $C_{20}$-$C_{24}$ substituted succinic anhydride and glycerin and or polyglycerol containing 2 to 6 glycerin units utilized as a process aid
[5]2,2'-azobis(2-methylbutyronitrile)

Table 2 summarizes the constituent components of the various polymers prepared in Examples 1 to 4.

TABLE 2

| Example No. | Composition[1] monomer/ (wt. %) | APE (wt. %)[2] |
| --- | --- | --- |
| 1 | NVP(84)/VA(15)/SMA(1) | 0.1 |
| 2 | NVP(84)/VA(15)/LMA(1) | 0.1 |
| 3 | NVP(64)/VA(35)/VA-10(1) | 0.1 |
| 4 | NVP(84)/VA(15)/VA-10(1) | — |

[1]Weight % of polymerized monomer repeating unit
[2]Based on the weight of the dry polymer
[3]Calculated by the method in Example 1

Example 5

This example illustrates the influence of crosslinked, nonionic, amphiphilic polymer prepared by dispersion polymerization on formulating a detersive composition with an anionic surfactant in water. Samples containing 2 wt. % polymer (total polymer solids) and 2 wt. % SLS surfactant (active material) in water are prepared using the polymers prepared in Examples 1 to 4. The yield stress, viscosity and shear thinning index of these polymers are determined by oscillatory and steady shear measurements on a controlled stress rheometer (TA Instruments AR1000N rheometer, New Castle, Del.) with cone and plate geometry (40 mm cone with a cone angle of 2 degrees and 56 µm gap) at 25° C. The oscillatory measurements are performed at a fixed frequency ranging from 1 Hz to 0.001 Hz. The elastic and viscous moduli (G' and G" respectively) are obtained as a function of increasing stress amplitude. In cases where the swollen polymer particles create a jammed network, G' is larger than G" at low stress amplitudes but decreases at higher amplitudes crossing G" because of rupture of the network. The stress corresponding to the crossover of G' and G" is noted as the yield stress. A plot of viscosity versus shear rate is obtained from the steady shear measurements. The viscosity at a shear rate of $3s^{-1}$ is noted. The shear thinning index is obtained from a power law fit ($\eta=K\gamma^{n-1}$) in the shear rate range 0.1 to 1 $s^{-1}$ where $\eta$ is viscosity, $\gamma$ is shear rate, n is the shear thinning index and K is a constant. The optical clarity (expressed as percent transmittance or % T) of the samples is measured using a Brinkmann PC 910 colorimeter with a 420 nm filter. The yield stress, viscosity, shear thinning index, and optical clarity values are set forth in Table 3.

TABLE 3

| Polymer No. | Yield Stress (Pa) | Viscosity (Pa · s) | Shear Thinning Index | % T |
|---|---|---|---|---|
| 1 | 1.9 | 1.4 | 0.3 | 85 |
| 2 | 2.9 | 1.6 | 0.29 | 86 |
| 3 | 0.6 | 0.8 | 0.4 | 94 |
| 4 | None | 0.015 | 1.0 | 99 |

It is clear that the yield stress fluids formulated with the polymers of Examples 1 to 3 display high yield stresses, good shear thinning indices and excellent optical clarity. The composition formulated with the linear polymer of Example 4 has no yield stress value. The linear polymers of the invention can be utilized to mitigate irritation induced by harsh surfactants where an increase in yield stress is undesirable.

Examples 6 to 8

The following polymers are prepared by a dispersion polymerization process similar to Examples 1 to 4. Monomers, cross-linkers and processing aids used in the polymerization are given in Table 4.

Table 5 summarizes the constituent components of the various polymers prepared in Examples 6 to 8.

TABLE 5

| Example No. | Composition Monomer (wt %) | APE (wt %)[2] |
|---|---|---|
| 6[1] | NVP(100) | 0.12 |
| 7 | NVP(82.5)/VA(14.5)/BEM(3) | 0.12 |
| 8 | NVP(82)/VA(14)/SMA(1)/BEM(3) | 0.12 |

[1]Comparative example
[2]Based on the weight of the dry polymer

Example 9

This example compares the performance of the hydrophilic homopolymer of comparative Example 6 with that of a polymer of the invention based on Example 7. Samples containing 2 wt. % polymer solids and 7 wt. % surfactant (a mixture of 5 wt. % Sulfochem™ ALS-K and 2 wt. % Chembetaine™ CAD based on active material) in water are prepared and the yield stress measured as in Example 5. It is found that the control sample exhibits a yield stress of only 0.1 Pa whereas the invention samples show a yield stress of at least 3.3 Pa.

The ability of a polymer system to suspend active and/or aesthetically pleasing insoluble oily, gaseous and particulate materials is important from the standpoint of product efficacy and appeal. The long-term suspension of 1.2 mm sized beads with specific gravity of approximately 1.4 (Unisphere™ REL 552 from Induchem AG, Switzerland) is examined in Examples 16 to 22. A six dram vial (approximately 70 mm high×25 mm in diameter) is filled to the 50 mm point with each formulation. The beads are weighed into each of the above sample formulations (0.6 wt. % based on the weight of the total formulation) and stirred gently with a wooden spatula until they are uniformly dispersed throughout each sample. The vials are placed on a lab bench at ambient room temperature to age for a 16 week period. The bead suspension property of each sample is monitored on a daily basis. The suspension results are visually observed over the 16 week test period. It is observed that the beads remain in suspension (do not rise or settle) in the formulations of the invention for over 4 months at room temperature but suspension is not achieved in the control sample wherein the beads settle to the bottom of the vial in 2 weeks.

Example 10

This example illustrates a composition containing a polymer of the invention prepared by the dispersion polymer-

TABLE 4

| Ex. No. | NVP (wt. %) | VA (wt. %) | SMA (wt. %) | BEM[1] (wt. %) | APE (wt. %)[2] | Stabilizer[3] (wt. %)[2] | PGS[4] (wt. %)[2] | CYCLO (wt. %)[2] | EtAc (wt. %)[2] | Initiator[5] (wt. %)[2] |
|---|---|---|---|---|---|---|---|---|---|---|
| 6[6] | 100 | — | — | — | 0.12 | — | — | 631 | 270 | 0.1 |
| 7 | 82.5 | 14.5 | — | 3 | 0.12 | 6 | 1 | 157 | 67 | 0.1 |
| 8 | 82 | 14 | 1 | 3 | 0.12 | 6 | 1 | 159 | 68 | 0.1 |

[1]Ethoxylated (25) Behenyl Methacrylate (Sipomer BEM from Rhodia)
[2]Based on the weight of the dry polymer
[3]50/30/20 (wt. %) copolymer of N-vinyl pyrrolidone/stearyl methacrylate/butyl methacrylate utilized as a dispersion polymerization stabilizer
[4]Reaction product $C_{20}$-$C_{24}$ substituted succinic anhydride and glycerin and or polyglycerol containing 2 to 6 glycerin units utilized as a process aid
[5]2,2'-azobis(2-methylbutyronitrile)
[6]Comparative example ization process (Example 8) with a surfactant mixture containing greater than 75 wt. % of an anionic ethoxylated surfactant. A sample containing 2.5 wt. % polymer solids and 14 wt % surfactant (12 wt % anionic ethoxylated surfactant Sulfochem™ ES-2 and 2 wt % amphoteric surfactant Chembetaine™ CAD based on active material) is prepared and the yield stresses measured as in Example 5. The sample exhibited a yield stress of 2.1 Pa.

Example 11

The components set forth in Table 6 are utilized to prepare a crosslinked, nonionic, amphiphilic dispersion polymer utilizing the method set forth for Examples 1 to 4. The quantities of these components are given in parts per hundred monomer (phm), unless otherwise specified. The final product is recovered as a fine powder after the polymerization solvent is removed by rotary evaporator under vacuum followed by a gentle milling process. The total polymer solids in the final dispersion is about 30 wt. %.

TABLE 6

| Example No. | NVP (phm) | VA (phm)[1] | BEM (phm)[1] | APE (phm)[2] | Stabilizer (phm)[2] | PGS[4] (phm)[2] | CYCLO (g) | Ethyl Acetate (g) | Initiator[5] (wt. %)[1] |
|---|---|---|---|---|---|---|---|---|---|
| 1 | 85 | 15 | 3 | 0.12 | 6 | 3 | 377 | 162 | 0.12 |

[1]Based on the weight of the total monomers
[2]Based on the dry weight of the polymer
[3]50/30/20 (wt. %) copolymer of N-vinyl pyrrolidone/stearyl methacrylate/butyl methacrylate employed as a polymeric dispersion stabilizer
[4]Reaction product $C_{20}$-$C_{24}$ substituted succinic anhydride and glycerin and or polyglycerol containing 2 to 6 glycerin units employed as a processing aid
[5]2,2'-azobis(2-methylbutyronitrile)

Example 12

Mitigation of skin irritancy induced by sodium dodecyl sulfate (SDS) surfactant dosed with the polymer of Example 11 is assessed in the Epiderm™ Human Tissue Model (EPI-200) bioassay conducted by MatTek Corporation, Ashland, Mass. The MatTek bioassay utilizes human derived epidermal keratinocytes (NHEK) which have been cultured to form a multilayered, highly differentiated model of the human epidermis. The model contains uniform and highly reproducible functional skin tissue layers (basal, spinous, granular, and cornified layers) corresponding to those found in vivo, and exhibits in vivo-like morphological and growth characteristics and is mitotically and metabolically active.

The Epiderm™ skin cultures treated with the SDS/polymer test formulation are evaluated by a MTT (3-[4,5-dimethylthiazol-2-yl]-2,5-diphenyltetrazolium bromide) tissue viability assay (MTT Effective Time-50 (ET-50) Protocol, MatTek Corporation) which assesses the potential irritancy mitigation (over a pre-determined exposure period) of test materials by assaying for MTT reduction in tissue cultures treated with SDS surfactant dosed with the test polymer relative to neat SDS surfactant control samples containing no polymer. The MTT tissue viability assay measures the NAD(P)H dependent microsomal enzyme reduction of MTT (and to a lesser extent, the succinate dehydrogenase reduction of MTT) after exposure to a treated skin culture test sample for various exposure times. The duration of exposure resulting in a 50% decrease in MTT conversion in test formulation treated EpiDerm™ cultures, relative to control cultures, is determined (ET-50).

A SDS surfactant/polymer test formulation is formulated from the components set forth in Table 10 and evaluated for irritancy potential using the MTT viability assay. Test samples containing neat SDS surfactant (no polymer) are formulated for comparative purposes.

TABLE 10

| Test Formulation | Polymer (wt. % active) | Surfactant (wt. % active) | D.I. Water |
|---|---|---|---|
| Example 11 | 2 | 2 | q.s. to 100 |
| Blank Surfactant | — | 2 | q.s. to 100 |

Skin tissue culture inserts (Cat. No. EPI-200) are pre-incubated in the wells of 6-well plates containing 0.9 ml of MatTek assay medium (Cat. No. EPI-100-ASY) for 1 hr. at 37° C. in a humidified atmosphere of 5% $CO_2$ in air. The 6-well plates containing the tissue culture inserts are removed from the incubator and the assay media is aspirated from the wells and replaced by an additional aliquot of 0.9 ml of pre-warmed (37° C.) assay media. For each exposure time wells are then dosed (2 repetitions) with 100 µl of the test formulations set forth in Table 10 (3 tissue culture wells are dosed with 100 µl ultra-pure water as a negative control for each of the test candidates). In addition, 100 µl of a positive control formulation (1% Triton X-100 in ultrapure water) is dosed into tissue culture wells (3 repetitions for each exposure time), as well as 3 repetitions of ultrapure water as a negative control. The exposure times of the test formulations, negative control and positive control are set forth below.

MTT assay plates are prepped by preparing a 24-well plate by adding 300 µl of MTT reagent solution to an appropriate number of wells to accommodate the test. The MTT reagent is utilized at a concentration of 1 mg/ml of MTT diluted in Dulbecco's Modified Eagle Medium (DMEM). The MTT/DMEM solution is centrifuged and decanted to remove any precipitate before use.

After exposure times of 60 (1 hr.), 120 (2 hrs.) and 210 (3.5 hrs.) minutes to the test solutions, the tissue cultures are removed from the incubator and thoroughly rinsed (2 times) with Dulbecco's phosphate buffered saline (DPBS) to remove the test material. The negative control is exposed for 4 hours and the positive control is exposed for time periods of 4, 6, 8, and 10 hours. Any remaining rinse media is decanted from the top of the tissue cultures. Each tissue culture insert is transferred to an appropriately labeled well of the 24-well plate containing the MTT reagent solution and placed back in the incubator. After 30 minutes reaction with the MTT reagent, the tissue cultures are removed from the incubator. Each tissue culture insert is removed from its well and the bottom is gently blotted with a lab tissue. The inserts are immersed into a labeled 24-well extraction plate containing 2 ml of isopropanol extractant solution. The 24-well extraction plate is covered with aluminum foil (to protect the samples from light) and placed into a sealable plastic bag to minimize evaporation of the extractant solution. The sealed 24-well extraction plate is set on an orbital shaker and gently shaken for 2 hours at ambient room temperature (approximately 20° C.).

Upon the conclusion of the extraction period, the extractant liquid within each tissue culture insert is decanted back into the well from which it was taken and thoroughly mixed with the extractant solution contained in the well. 200 µl of the mixed extractant solution in each well is transferred into a 96-well microtiter plate for spectrophotometric analysis. A 200 µl sample of neat extractant solution (isopropanol) is utilized as a blank. The absorbance (optical density) at 570 nm ($OD_{570}$) of the extracted samples in each well is measured with a spectrophotometer (EMax® Microplate Reader, Molecular Devices, LLC, Sunnyvale, Calif.) equipped with a 96-well plate reader and no reference filter. Background noise in all samples is subtracted to improve the quality of the acquired data. The mean $OD_{570}$ values of the polymer test wells, blank surfactant test wells, negative control wells and positive control for each exposure time are calculated. The percent viability of each sample is calculated utilizing the formula:

% viability=(ave.) $OD_{570}$ of Test Sample/(ave.) $OD_{570}$ of Negative Control Sample×100

Viabilities are determined using the MTT assay and the exposure time which reduces tissue viability to 50% (ET-50). ET-50 values for each tested formulation are determined mathematically using a spreadsheet which interpolates between exposure times that brackets 50% viability. The results for each formulation are presented in the spreadsheets set forth in the tables below.

TABLE 11

(Polymer + Surfactant)

| Exposure Time (hr) | Test Well | OD (570 nm) | Ave. (OD) | Viability (%) |
|---|---|---|---|---|
| 1 | Rep 1 | 1.489 | 1.373 | 134.8[1] |
|   | Rep 2 | 1.256 |   |   |
| 2 | Rep 1 | 0.648 | 0.713 | 70.0 |
|   | Rep 2 | 0.777 |   |   |
| 3.5 | Rep 1 | 0.226 | 0.229 | 22.5 |
|   | Rep 2 | 0.232 |   |   |
| H$_2$O | Rep 1 | 1.017 | 1.018 | 100.0 |
|   | Rep 2 | 1.001 |   |   |
|   | Rep 3 | 1.036 |   |   |
| ET-50 (hr) | 2.53 |   |   |   |

[1]Temporary hormesis effect

TABLE 12

(Neat Surfactant)

| Exposure Time (hr) | Test Well | OD (570 nm) | Ave. (OD) | Viability (%) |
|---|---|---|---|---|
| 1 | Rep 1 | 1.074 | 0.940 | 92.3 |
|   | Rep 2 | 0.805 |   |   |
| 2 | Rep 1 | 0.363 | 0.329 | 32.3 |
|   | Rep 2 | 0.294 |   |   |
| 3.5 | Rep 1 | 0.161 | 0.169 | 16.6 |
|   | Rep 2 | 0.177 |   |   |
| H$_2$O | Rep 1 | 1.017 | 1.018 | 100 |
|   | Rep 2 | 1.001 |   |   |
|   | Rep 3 | 1.036 |   |   |
| ET-50 (hr) | 1.63 |   |   |   |

TABLE 13

(1% Triton X-100)

| Exposure Time (hr) | Test Well | OD (570 nm) | Ave. (OD) | Viability (%) |
|---|---|---|---|---|
| 4 | Rep 1 | 1.206 | 1.250 | 74.3 |
|   | Rep 2 | 1.244 |   |   |
|   | Rep 3 | 1.301 |   |   |
| 6 | Rep 1 | 0.68 | 0.830 | 49.3 |
|   | Rep 2 | 0.983 |   |   |
|   | Rep 3 | 0.827 |   |   |
| 8 | Rep 1 | 0.211 | 0.233 | 13.9 |
|   | Rep 2 | 0.266 |   |   |
|   | Rep 3 | 0.223 |   |   |
| 10 | Rep 1 | 0.21 | 0.218 | 13.0 |
|   | Rep 2 | 0.229 |   |   |
|   | Rep 3 | 0.215 |   |   |
| H$_2$O | Rep 1 | 1.596 | 1.683 | 100.0 |
|   | Rep 2 | 1.697 |   |   |
|   | Rep 3 | 1.756 |   |   |
| ET-50 (hr) | 5.93 |   |   |   |

Based on longer ET-50 values, anionic surfactant formulations containing the polymers of the invention are less irritating (ET-50=2.53 hrs.) than the same concentrations of neat (without polymer) anionic surfactant (ET-50=1.63 hrs.). The ET-50 value of 5.93 hrs. for the positive control (1% Triton X-100) fell within two standard deviations of the historical mean (4.77 to 8.72 hrs.), thereby meeting the acceptance value.

What is claimed is:

1. A method for mitigating ocular and/or skin irritation induced by detersive compositions containing at least one anionic surfactant said method comprising contacting the skin with a detersive composition comprising a crosslinked nonionic amphiphilic dispersion polymer prepared from a free radically polymerizable monomer mixture comprising:
  i) 60 to 90 wt. % of N-vinyl pyrrolidone (based on the total monomer wt.);
  ii) 10 to 35 wt. % of at least one vinyl ester selected from vinyl acetate, vinyl propionate, vinyl butyrate, vinyl isobutyrate, vinyl valerate, vinyl hexanoate, vinyl 2-methylhexanate, vinyl 2-ethylhexanoate, vinyl iso-octanoate, vinyl nonanoate, vinyl neodecanoate, vinyl decanoate, vinyl versatate, vinyl laurate, vinyl palmitate, and vinyl stearate;
  iii) 0 or 0.5 to 5 wt. % of an $C_8$-$C_{22}$ alkyl (meth)acrylate selected from octyl (meth)acrylate, 2-ethylhexyl (meth)acrylate, decyl (meth)acrylate, isodecyl (meth)acrylate, lauryl (meth)acrylate, tetradecyl (meth)acrylate, hexadecyl (meth)acrylate, stearyl (meth)acrylate, and behenyl (meth)acrylate; and
  iv) 0 or 0.5 to 4.5 wt. % of at least one associative monomer and/or semi-hydrophobic monomer (said weight percent is based on the weight of the total monomers)
  v) 0.01 to 1 wt. % in one aspect or from 0.1 to 0.3 wt. % of at least one crosslinker (based on the dry weight of the polymer), wherein said detersive composition comprises;
  a) water;
  b) 1 to 5 wt. % of said crosslinked nonionic amphiphilic dispersion polymer;
  c) 6 to 20 wt. % of a surfactant mixture containing an anionic surfactant and an amphoteric surfactant; subject to the proviso that at least one of monomers iii) and iv) must be present and when both monomers iii) and iv) are present in said monomer mixture, the combined weight of said monomers iii) and iv) cannot exceed 5 wt. % of the weight of the total monomer mixture;

wherein said associative monomer is represented by formula VIIB:

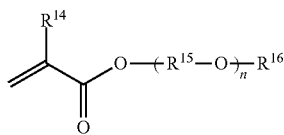

VIIB $R^{14}$ is hydrogen or methyl; $R^{15}$ is a divalent alkylene moiety independently selected from $C_2H_4$, $C_3H_6$, and $C_4H_8$, and n represents an integer ranging from about 10 to about 60, ($R^{15}$—O) can be arranged in a random or a block configuration; $R^{16}$ is a substituted or unsubstituted alkyl selected from a $C_8$-$C_{30}$ linear alkyl, a $C_8$-$C_{30}$ branched alkyl, a $C_8$-$C_{30}$ carbocyclic alkyl, a $C_2$-$C_{30}$ alkyl-substituted phenyl, an araalkyl substituted phenyl, and an aryl-substituted $C_2$-$C_{30}$ alkyl, wherein the $R^{16}$ alkyl group, aryl group, phenyl group optionally comprises one or more substituents selected from the group consisting of a hydroxyl group, an alkoxyl group, benzyl group styryl group, and a halogen group; and wherein said semi-hydrophobic monomer is selected from at least one monomer represented by formulas VIIIA and VIIIB:

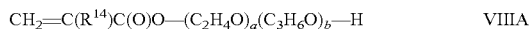

VIIIA

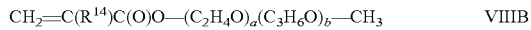

VIIIB $R^{14}$ is hydrogen or methyl, and "a" is an integer ranging from 0 or 2 to about 120 in one aspect, from about 5 to about 45 in another aspect, and from about 10 to about 0.25 in a further aspect, and "b" is an integer ranging from about 0 or 2 to about 120 in one aspect, from about 5 to about 45 in another aspect, and from about 10 to about 0.25 in a further aspect, subject to the proviso that "a" and "b" cannot be 0 at the same time.

2. The method of claim 1 wherein said at least one vinyl ester is selected from vinyl acetate, vinyl decanoate, or mixtures thereof.

3. The method of claim 1 wherein said at least one associative monomer is behenyl polyethoxylated methacrylate, and said semi-hydrophobic monomer is methoxy polyethyleneglycol methacrylate.

4. The method of claim 1 wherein said at least one $C_8$-$C_{22}$ alkyl (meth)acrylate monomer is selected from lauryl methacrylate, stearyl methacrylate, or mixtures thereof.

5. The method of claim 3 wherein said associative and/or semi-hydrophobic monomer contains 2 to 30 moles of ethoxylation.

6. The method of claim 1 wherein said anionic surfactant contains an average of 1 to 3 moles of ethoxylation.

7. The method of claim 1 wherein the ratio of said anionic surfactant to said amphoteric surfactant ranges from about 10:1 to about 2:1 (wt./wt.).

8. The method of claim 7 wherein said anionic surfactant is selected from the sodium or ammonium salts of dodecyl sulfate, lauryl sulfate, laureth sulfate, or mixtures thereof.

9. The method of claim 7 wherein said amphoteric surfactant is cocamidopropyl betaine.

10. The method of claim 1 wherein said associative monomer is selected from lauryl polyethoxylated (meth)acrylate, cetyl polyethoxylated (meth)acrylate, cetearyl polyethoxylated (meth)acrylate, stearyl polyethoxylated (meth)acrylate, arachidyl polyethoxylated (meth)acrylate, behenyl polyethoxylated (meth)acrylate, cerotyl polyethoxylated (meth)acrylate, montanyl polyethoxylated (meth)acrylate, melissyl polyethoxylated (meth)acrylate, where the polyethoxylated portion of the monomer contains about 2 to about 50 ethylene oxide units, and said semi-hydrophobic monomer is selected from methoxy polyethyleneglycol (meth)acrylate or polyethyleneglycol (meth)acrylate, where the polyethoxylated portion of the monomer contains about 2 to about 50 ethylene oxide units.

11. The method of claim 1 wherein said crosslinker is selected from a monomer having an average of 3 crosslinkable unsaturated functional groups.

12. The method of claim 1 wherein said crosslinker is pentaerythritol triallyl ether.

13. The method of claim 1 wherein said dispersion polymer is prepared in the presence of a steric stabilizer polymer.

14. The method of claim 13 wherein said steric stabilizer is selected from a copolymer of N-vinyl pyrrolidone/stearyl methacrylate/butyl acrylate, the ester of the reaction product of a $C_{20}$ to $C_{24}$ alkyl substituted succinic anhydride and a polyol selected from glycerin and/or a polyglycerol containing 2 to 6 glycerin units, and mixtures thereof.

15. The method of claim 1 wherein said detersive composition is selected from shampoos, baby shampoos, body washes, shower gels, liquid hand soaps, liquid dishwashing detergents, pet cleansing product, moist cleansing wipes, or facial cleansers.

* * * * *